(12) United States Patent
Van Lier et al.

(10) Patent No.: US 7,541,457 B2
(45) Date of Patent: Jun. 2, 2009

(54) AMPHIPHILIC TRISULFONATED PORPHYRAZINES FOR PHOTODYNAMIC APPLICATIONS IN MEDICINE

(75) Inventors: Johannes E. Van Lier, North Hatley (CA); Haroutioun Minas Hasséssian, Montreal (CA); Hongjian Tian, Mississauga (CA); Nicole Cauchon, Sherbrooke (CA); Hasrat Ali, Lennoxville (CA)

(73) Assignee: Universite de Sherbrooke, Sherbrooke, Quebec (CA)

( * ) Notice: Subject to any disclaimer, the term of this patent is extended or adjusted under 35 U.S.C. 154(b) by 502 days.

(21) Appl. No.: 10/556,590

(22) PCT Filed: May 14, 2004

(86) PCT No.: PCT/CA2004/000739

§ 371 (c)(1),
(2), (4) Date: Feb. 14, 2006

(87) PCT Pub. No.: WO2004/101516

PCT Pub. Date: Nov. 25, 2004

(65) Prior Publication Data

US 2006/0282038 A1 Dec. 14, 2006

Related U.S. Application Data

(60) Provisional application No. 60/470,197, filed on May 14, 2003.

(51) Int. Cl.
*C09B 47/24* (2006.01)
(52) U.S. Cl. .................. 540/123; 540/132; 436/548
(58) Field of Classification Search ................. 540/123, 540/132; 436/548
See application file for complete search history.

(56) References Cited

U.S. PATENT DOCUMENTS 5,756,541 A 5/1998 Strong et al.
5,864,044 A 1/1999 Van Lier et al.

FOREIGN PATENT DOCUMENTS

WO    WO-01/42368 A    6/2001

OTHER PUBLICATIONS

Tian et al. "Synthesis of water soluble trisulfonated phthalocyanines via palladium-catalysed cross coupling reactions" Tetrahedron Letters, 2000, vol. 41, pp. 8435-8438.*
Margaron, P et al., Photochemistry and Photobiology, vol. 63, No. 2, 1996, pp. 217-223.
Oleinick, N.L., et al., Photochem. Photobiol. Sci., vol. 1, 2002, pp. 1-21.
Quam, T. et al., Investigative Ophthalmology & Visual Science, vol. 42, No. 10, Sep. 2001, pp. 2408-2413.
Sharman, W.M. et al., DDT, vol. 4, No. 11, Nov. 1999, pp. 507-517.
Tian, H. et al., Tetrahedron Letters, vol. 41, 2000, pp. 8435-8438.
Li, Z et al., Canadian Journal of Chemistry, vol. 77, No. 1, 1999, pp. 138-145.
Database Beilstein, Beilstein Institute for Organic Chemistry, Frankfurt-Main, De; Citation No. 6187722, XP002295842, Beilstein Registry No. 8333585 and Beilstein Reaction ID 5201875.
Ottoni, O et al., Tetrahedron, Elsevier Science Publishers, Amsterdam, NL, vol. 54, No. 46, Nov. 12, 1998, pp. 13915-13928.
Artico, M et al., Journal of Medicinal Chemistry, American Chemical Society, Washington, US, vol. 39, No. 2, Jan. 19, 1996, pp. 522-530.
Kudrevich, S et al., Journal of Medicinal Chemistry, Nov. 21, 1997, vol. 40, No. 24, pp. 3897-3904.
Kliesh, H. et al., Liebigs Annalen: Organic and Bioorganic Chemistry, VCH Publishers, US, No. 10, Oct. 1995, pp. 1269-1274.
Aoudia, M. et al., Journal of the American Chemical Society, American Chemical Society, Washington, DC, US, vol. 119, No. 26, 1997, pp. 6029-6039.

* cited by examiner

*Primary Examiner*—Rei-Tsang Shiao
*Assistant Examiner*—Joseph R Kosack
(74) *Attorney, Agent, or Firm*—Birch Stewart Kolasch & Birch, LLP

(57) ABSTRACT

Disclosed herein are novel trisulfonated tribenzo-mononahpto-porphyrazines, processes for making them and their application as improved photosensitizing drugs for the treatment of various medical conditions by photodynamic therapy (PDT). These water-soluble amphiphilic porphyrazines are substituted with different alkylyl, aryl, aminoalkyl and aminoaryl groups, with or without carboxyl moeity.

19 Claims, 11 Drawing Sheets

(NVT-0275)

(NVT-0275+Albumin)

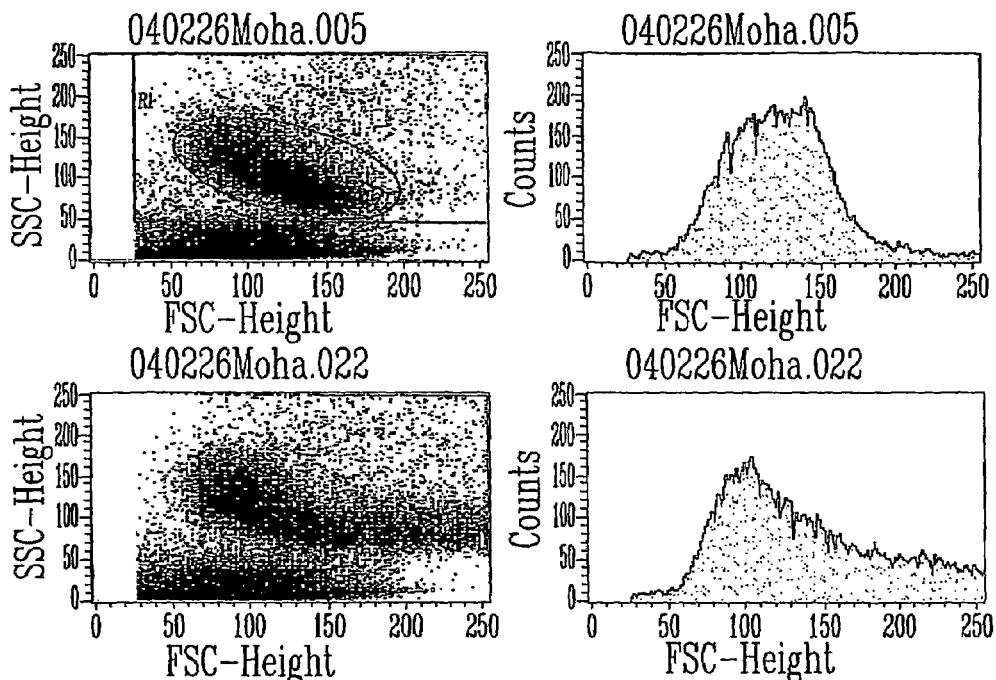

Region Statistics
File: 040226Moha.005                Log Data Units: Linear Values
Sample ID:                          Patient ID:
Tube: Untitled                      Panel: Untitled Acquisition Tube List
Acquisition Date: 26-Fed-04         Gate: No Gate
Gated Events: 80709                 Total Events: 80709
X Parameter: FSC-Height (Linear)    Y Parameter: SSC-Height (Linear)

| Region | Events | % Gated | % Total | X Mean | X Geo Mean | Y Mean | Y Geo Mean | Px,Py |
|---|---|---|---|---|---|---|---|---|
| R1 | 12469 | 15.45 | 15.45 | 121.47 | 118.45 | 104.61 | 101.12 | 1,2 |
| R2 | 14938 | 18.51 | 18.51 | 125.71 | 120.22 | 113.12 | 105.71 | 1,2 |

Region Statistics
File: 040226Moha.022                Log Data Units: Linear Values
Sample ID:                          Patient ID:
Tube: Untitled                      Panel: Untitled Acquisition Tube List
Acquisition Date: 26-Fed-04         Gate: No Gate
Gated Events: 85256                 Total Events: 85256
X Parameter: FSC-Height (Linear)    Y Parameter: SSC-Height (Linear)

| Region | Events | % Gated | % Total | X Mean | X Geo Mean | Y Mean | Y Geo Mean | Px,Py |
|---|---|---|---|---|---|---|---|---|
| R1 | 10553 | 12.38 | 12.38 | 120.73 | 116.44 | 109.19 | 105.79 | 1,2 |
| R2 | 15755 | 18.48 | 18.48 | 144.37 | 133.41 | 115.37 | 107.73 | 1,2 |

Fig-8

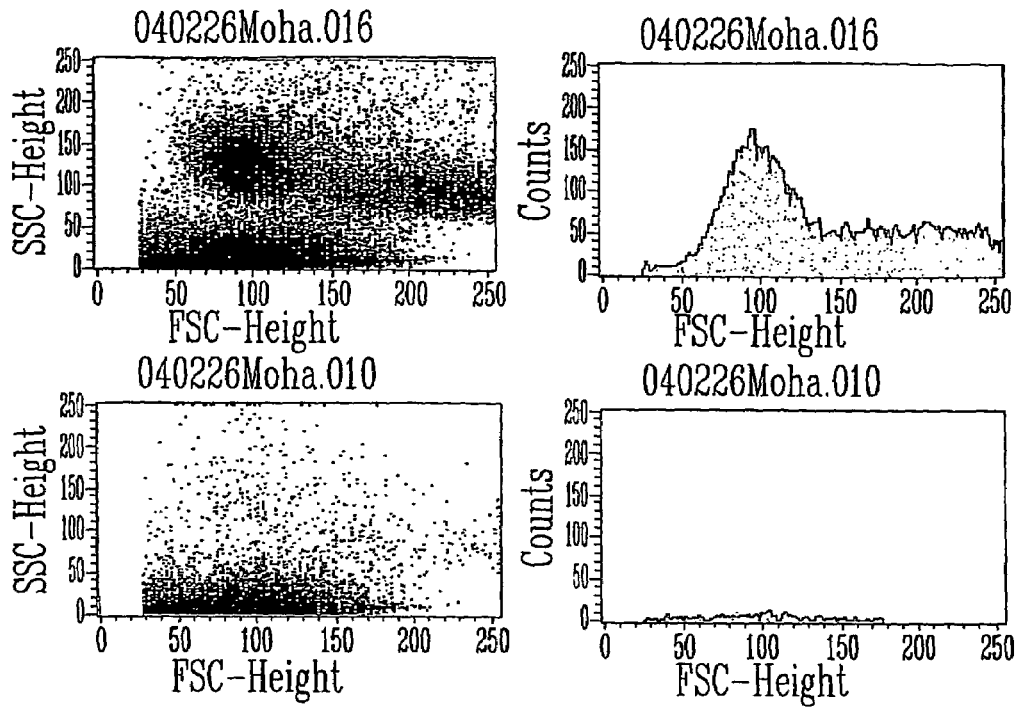

Region Statistics

File: 040226Moha.016  
Sample ID:  
Tube: Untitled  
Acquisition Date: 26-Fed-04  
Gated Events: 85104  
X Parameter: FSC-Height (Linear)

Log Data Units: Linear Values  
Patient ID:  
Panel: Untitled Acquisition Tube List  
Gate: No Gate  
Total Events: 85104  
Y Parameter: SSC-Height (Linear)

| Region | Events | % Gated | % Total | X Mean | X Geo Mean | Y Mean | Y Geo Mean | Px,Py |
|---|---|---|---|---|---|---|---|---|
| R1 | 8963 | 10.15 | 10.15 | 115.73 | 111.20 | 118.66 | 115.40 | 1,2 |
| R2 | 14769 | 17.35 | 17.35 | 148.20 | 135.18 | 119.58 | 112.58 | 1,2 |

Region Statistics

File: 040226Moha.010  
Sample ID:  
Tube: Untitled  
Acquisition Date: 26-Fed-04  
Gated Events: 104258  
X Parameter: FSC-Height (Linear)

Log Data Units: Linear Values  
Patient ID:  
Panel: Untitled Acquisition Tube List  
Gate: No Gate  
Total Events: 104258  
Y Parameter: SSC-Height (Linear)

| Region | Events | % Gated | % Total | X Mean | X Geo Mean | Y Mean | Y Geo Mean | Px,Py |
|---|---|---|---|---|---|---|---|---|
| R1 | 377 | 0.36 | 0.36 | 127.13 | 122.57 | 102.30 | 96.96 | 1,2 |
| R2 | 912 | 0.87 | 0.87 | 125.58 | 112.31 | 100.28 | 89.02 | 1,2 |

Fig. 8 (CONTINUED)

AMPHIPHILIC TRISULFONATED PORPHYRAZINES FOR PHOTODYNAMIC APPLICATIONS IN MEDICINE

TECHNICAL FIELD

The present invention relates to novel trisulfonated tribenzo-mononahptho-porphyrazines, processes for making them and their application as improved photosensitizing drugs for the treatment of various medical conditions by photodynamic therapy (PDT).

BACKGROUND OF THE INVENTION

Photodynamic therapy (PDT) of various medical conditions usually involves i.v. administration of a photosensitizer, followed (after several hours up to a day) by the illumination of the affected tissue with red light. This results in activation of the sensitizer and subsequently the formation of reactive oxygen species (ROS), particularly singlet oxygen. Depending on the localization of the photosensitizer, the ensuing oxidative stress leads to vascular collapse and cell death involving apoptosis or necrosis (Oleinick et al., *Photochem. Photobiol. Sci.*, 1: 1-22, 2002). Most photosensitizers currently in clinical use or in trials have one of the following drawbacks, or a combination thereof (Sharman et al., *Drug Discovery Today*, 4; 507-517, 1999): they consist of a mixture of products, they are lipophilic drugs, requiring formulation in liposomes or an emulsion, their photochemical properties are not optimal for PDT, their pharmacokinetics and target localization are not compatible with the selected application.

During the past decades phthalocyanines (Pc) and their derivatives have been extensively studied. Pc and their derivatives found numerous applications in widely different areas due to their distinct properties. Both lipid and water-soluble Pc have been advanced as photosensitizers for the photodynamic therapy (PDT) of cancer. Among the water-soluble derivatives particularly the efficacy of sulfonated metallo Pc has been studied. Depending on the degree of sulfonation, Pc exhibit varying hydrophobic and hydrophilic properties inducing different photodynamic effects. Adjacently substituted, disulfonated compounds have the appropriate amphiphilic properties for optimal cell membrane penetration, resulting in high photodynamic activity against tumor cells (Margaron et al., *Photochemistry and photobiology*, 63(2):217-223, 1996). Inherent to the classical procedure of their preparation, such derivatives are difficult to purify as single isomeric products and as such not suitable for human applications.

A particularly interesting application of PDT involves the treatment of wet age-related macular degeneration (AMD). Wet AMD is the leading cause of blindness for people over the age of 50 and involves the rapid growth of abnormal blood vessels under the central retina. Leakage from these abnormal vessels causes scarring and an accelerated loss of visual acuity. The retina is protected by a blood retinal barrier (BRB) constituted by two spatially distinct monolayers of cells, of which the tight junctions between retinal capillary endothelial cells forms the inner retinal barrier, and the retinal pigment epithelium forms the outer barrier. The BRB serves to keep the retina dry and preserves the ionic balance of the retina. In addition, some circulating factors may be toxic to the retina and are kept out by the BRB. Thus an intact BRB is essential for the normal function of the retina.

The BRB is breached in many retinopathies involving vascular disorders including macular degeneration, diabetic retinopathy, exudative retinal detachment, Coat's disease and various forms of macular edema. Plasma extravasation is a direct consequence of the BRB breakdown. Plasma extravasation results in the deposit of material, which is normally within the lumen of vessels onto the retina, resulting in the loss of vision at such sites due to obstruction of light transmission. Subretinal edema brought about by plasma extravasation will lead to detachment of essential cellular connections resulting in vision loss.

Evidence shows that Vascular Endothelial Growth Factor (VEGF), originally known as vascular permeability factor, is a key element in the breakdown of the BRB under pathological conditions (Quam, et al., *Invest. Ophth. Visual Sci.*, 42: 2408-2413, 2001). Photodynamic therapy using a benzoporphyrin derivative (verteporfin) as a photosensitizer has been shown to be an efficient procedure to close the abnormal vessels, and has been accepted in several countries for the treatment of AMD (U.S. Pat. No. 5,756,541).

In a search for phthalocyanine-like structures that exhibit similar amphiphilic and cell penetrating properties as those of the disulfonated Pc, the synthesis and properties of trisulfonated Pc substituted with a lipophilic group on the fourth non-sulfonated benzyl group were previously investigated. In a first approach boron(III) subphthalocyanines were used as intermediates (U.S. Pat. No. 5,864,044). The success of this procedure depends dramatically on the nature of the substituents on the subPc, as well as other factors, and as such the procedure was found not to be suitable for the preparation of trisulfonated Pc with extended lipophilic substituents. Subsequently, it was found that such compounds could be obtained via palladium-catalyzed cross coupling reactions using a monoiodo trisulfonated Pc as starting material (Tian et al., *Tetrahedron Lett.*, 41: 8435-8438, 2000). Such mono functionalized trisulfonated Pc exhibit the typical Q band near 680 nm.

It would be highly desirable to be provided with novel water-soluble amphiphilic photosensitizing drugs for the treatment of various medical conditions by photodynamic therapy (PDT) that overcome the drawbacks of the prior art compounds.

It would also be highly desirable to be provided with novel tri-(sulfobenzo)-mono-(carboxyl-naphtho)-porphyrazines compounds for attachment to a protein carrier such as an antibody, preferably a monoclonal antibody (Mab) or its fragments for the treatment of various medical conditions by PDT.

SUMMARY OF THE INVENTION

One aim of the present invention is to provide novel trisulfonated tribenzo-mononahptho-porphyrazines, as improved photosensitizing drugs for the treatment of various medical conditions by photodynamic therapy (PDT).

Another aim of the present invention is to provide processes for making these novel trisulfonated tribenzo-mononahptho-porphyrazines and their application.

Another aim of the present invention is to provide novel tri-(sulfobenzo)-mono-(carboxyl-naphtho)-porphyrazines compounds for attachment to a protein carrier such as an antibody, preferably a monoclonal antibody (Mab) or its fragments and their application.

In accordance with the present invention there is provided a method for preparing a purified compound of formula (I), comprising the steps of:

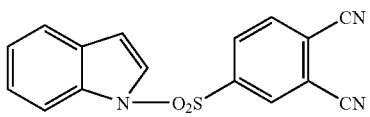
(I)

a) mixing KOH with tetrabutyl ammonium hydrogen sulfate;
b) adding indole to the mixture of step a);
c) adding sulfonyl chloride to the mixture of step b) to obtain the compound of formula (I);
d) removing solid KOH from the mixture of step c);
e) washing the mixture of step d); and
f) drying the compound of formula (I).

In accordance with the present invention, there is also provided an intermediate compound consisting of a 5- or 6-substituted tri-[4-(1-indolylsulfobenzo)]-mono-naphtho-porphyrazine compound of formula (II):

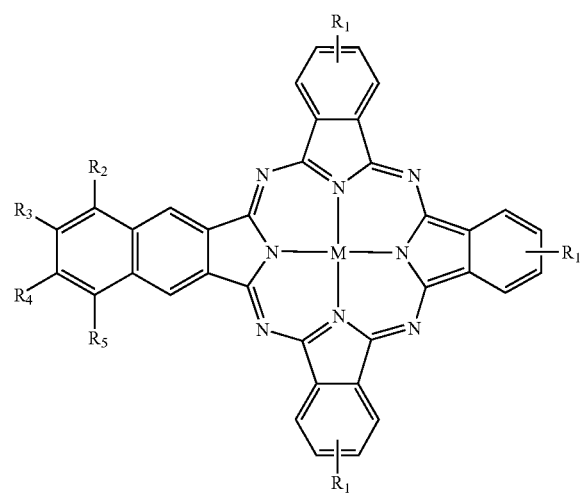
(II)

Wherein
$R_1$ is

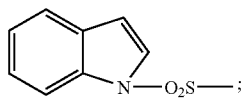

M is H . . . H or a metal; and
$R_3$, $R_4$ and $R_5$ are hydrogen when $R_2$ is an —C≡CX or —NHX when X is an alkyl, an aryl, an alkylcarboxyl or an arylcarboxyl; or
$R_2$, $R_4$ and $R_5$ are hydrogen when $R_3$ is an —C≡CX or —NHX when X is an alkyl, an aryl, an alkylcarboxyl or an arylcarboxyl.

Still in accordance with the present invention, there is also provided a water-soluble compound of formula (III):

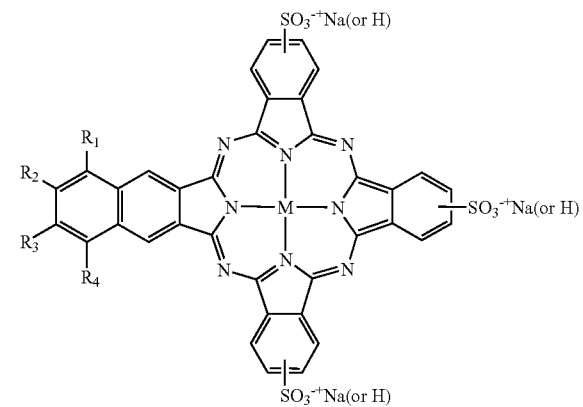
(III)

Wherein
M is H . . . H or a metal, such as for example Zn, Co(II), Ni and Cu; and
$R_2$, $R_3$ and $R_4$ are hydrogen when $R_1$ is an —C≡CX or —NHX when X is an alkyl, an aryl, an alkylcarboxyl or an arylcarboxyl; or
$R_1$, $R_3$ and $R_4$ are hydrogen when $R_2$ is an —C≡CX or —NHX when X is an alkyl, an aryl, an alkylcarboxyl or an arylcarboxyl.

Further in accordance with the present invention, there is provided a method for preparing the compound of formula (II) as described above. The method comprises the step of condensing together iodo-2,3-dicyanonaphthalene with indole protected 3,4-dicyanophenylsulfonyl in the presence of $CH_3COOM$, to obtain the compound of formula (II). The method may additionally comprise the step of purifying the compound of formula (II), such as by chromatography or silica gel column chromatography.

The method may also comprise the step of cleaving off the indole contained in $R_1$ of the compound of formula (II) to obtain a water-soluble 5- or 6-substituted tri-(4-sulfobenzo)-mono-naphtho-porphyrazine compound of formula (III)

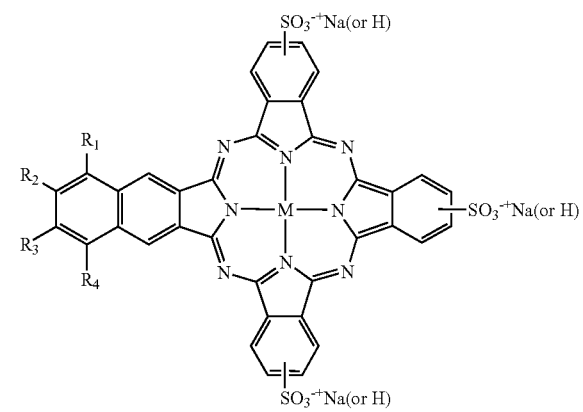
(III)

Wherein
M is H . . . HH or a metal selected from the group consisting of Zn, Co(II), Ni and Cu; and $R_2$, $R_3$ and $R_4$ are hydrogen when $R_1$ is an —C≡CX or —NHX when X is an alkyl, an aryl, an alkylcarboxyl or an arylcarboxyl; or $R_1$, $R_3$ and $R_4$ are hydrogen when $R_2$ is an —C≡CX or —NHX when X is an alkyl, an aryl, an alkylcarboxyl or an arylcarboxyl.

The compound of formula (III) may further be purified by for example chromatography such as silica gel column chromatography.

Also in accordance with the present invention, there is provided the use of the compounds defined above in conjunction with light of appropriate wavelength for photodynamic therapy (PDT).

Still in accordance with the present invention, there is provided the use of Zinc tri-(4-sulfobenzo)-5-mono-[(1-hexynyl)naphtho]-porphyrazine for the treatment of light accessible cancers in conjunctions with light of appropriate wavelength or for the treatment of age related macular degeneration (AMD) in conjunctions with light of appropriate wavelength.

Still in accordance with the present invention, there is provided an intermediate compound selected from the group consisting of formula (6),

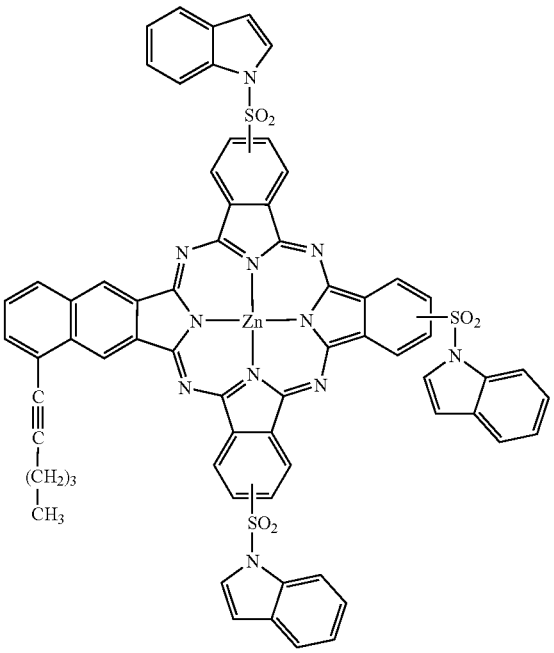

an intermediate compound of formula (21):

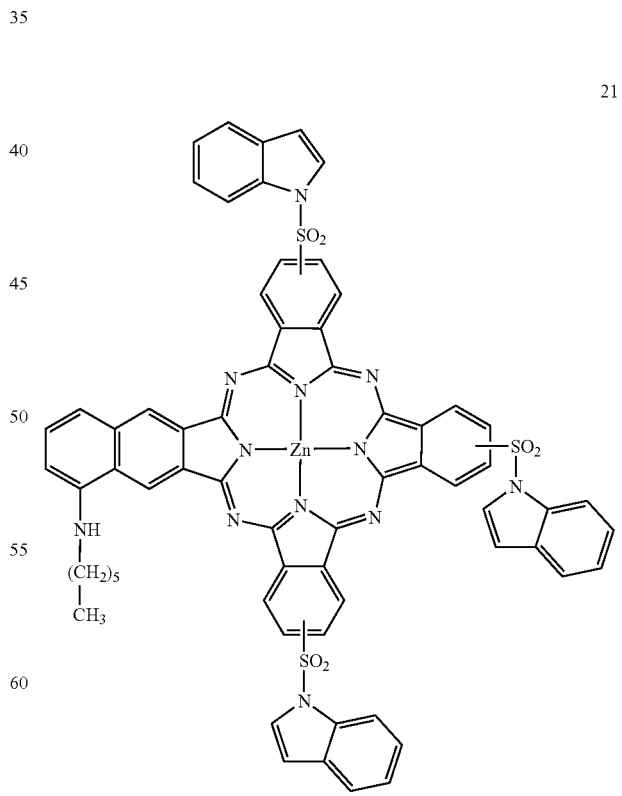

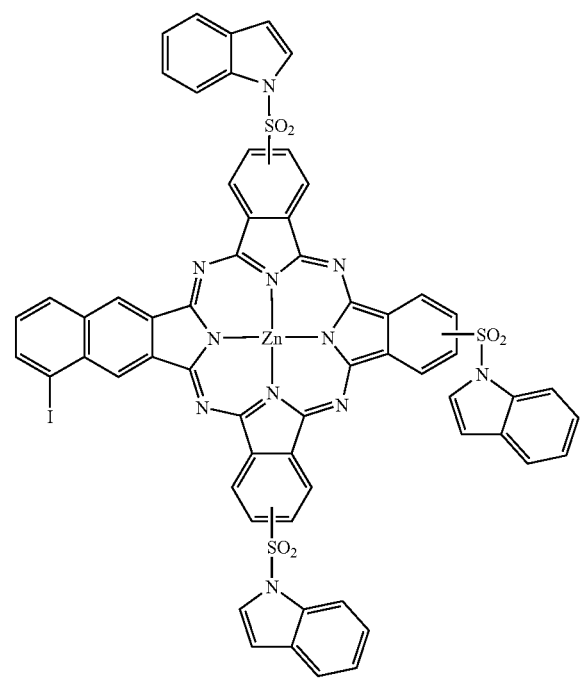

an intermediate compound of formula (16):

an intermediate compound of formula (76):

a compound of formula (46):

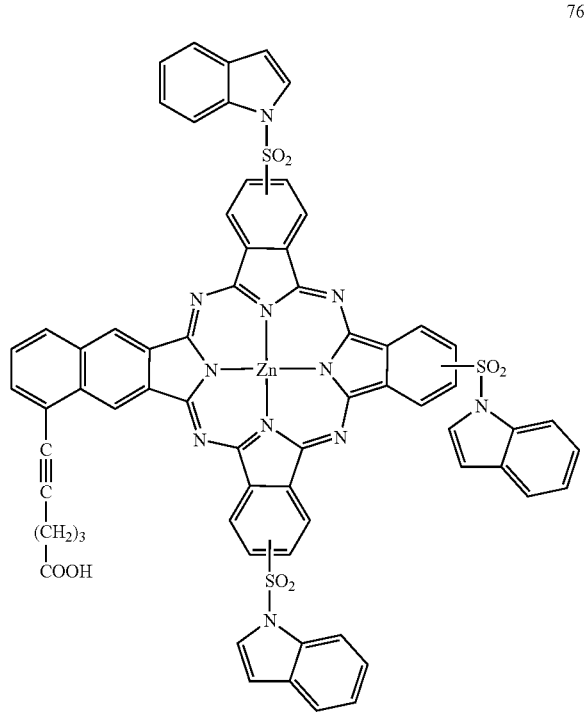

a compound of formula (51):

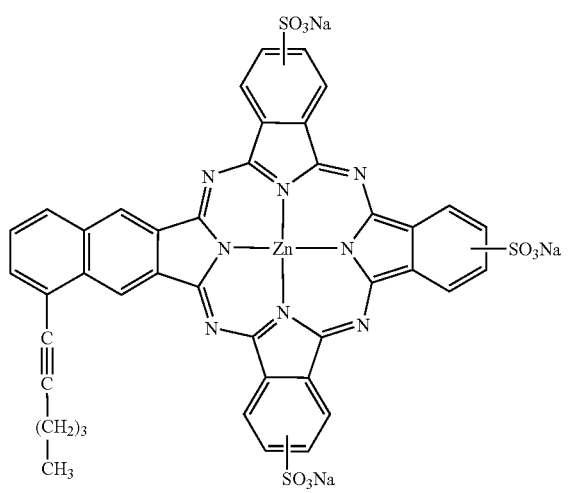

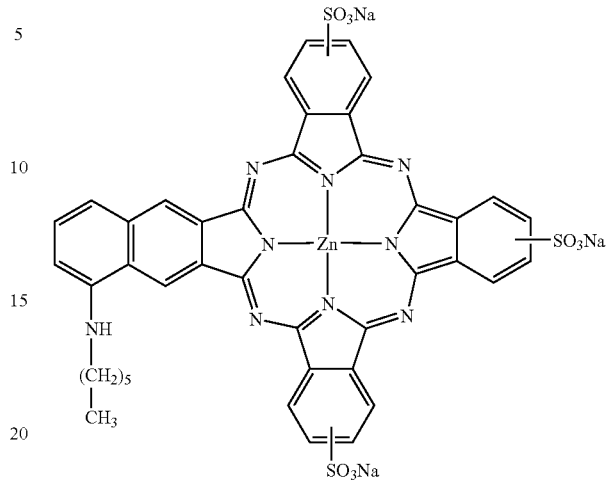

and
a compound of formula (106):

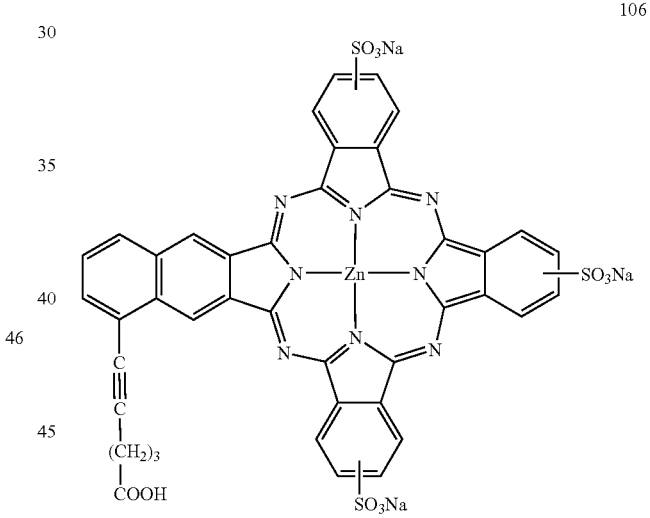

Further in accordance with the present invention, there is also provided a conjugate comprising any of the aforementioned compound conjugated to a protein carrier, such as an antibody or a monoclonal antibody.

The present invention also provides for the use of any of these compounds or conjugates in conjunction with light of appropriate wavelength for photodynamic therapy (PDT).

Still in accordance with the present invention, there is provided the use of any one of the aforementioned compounds or conjugates, or a pharmaceutically acceptable salt thereof, for the treatment of a condition selected from the group consisting of a light accessible cancer, an ocular disease, extravasation (such as plasma extravasation) and a leaky blood vessel and non-ocular vascular disease in conjunction with light of appropriate wavelength. Alternatively, any one of the aforementioned compounds or conjugates, or a pharmaceutically acceptable salt thereof, can also be used in the manufacture of a medicament for any of the aforementioned treatments Also in accordance with the present invention, there is provided a method of treating a condition selected from the group consisting of a light accessible cancer, an ocular disease, extravasation and a leaky blood vessel and non-ocular vascular disease in an individual comprising:
 a) administering an effective amount of any one of the aforementioned compounds of conjugates, or a pharmaceutically acceptable salt thereof; and
 b) irradiating the individual with light of appropriate wavelength at a site effected by the condition.

In accordance with the present invention, there is also provided the use of zinc tri-(4-sulfobenzo)-5-mono-[(1-hexynyl)naphtho]-porphyrazine or a pharmaceutically acceptable salt thereof for the treatment of a condition selected from the group consisting of a light accessible cancer, an ocular disease, extravasation and a leaky blood vessel and non-ocular vascular disease in conjunction with light of appropriate wavelength.

There is also provided in accordance with the present invention the use of zinc tri-(4-sulfobenzo)-5-mono-[(1-hexynyl)naphtho]-porphyrazine or a pharmaceutically acceptable salt thereof in the manufacture of a medicament to treat a condition selected from the group consisting of a light accessible cancer, an ocular disease, extravasation and a leaky blood vessel and non-ocular vascular disease in conjunction with light of appropriate wavelength.

Still in accordance with the present invention, there is provided a method of treating a condition selected from the group consisting of a light accessible cancer, an ocular disease, extravasation and a leaky blood vessel and non-ocular vascular disease in an individual comprising:
 a) administering an effective amount of zinc tri-(4-sulfobenzo)-5-mono-[(1-hexynyl)naphtho]-porphyrazine or a pharmaceutically acceptable salt thereof; and
 b) irradiating the individual with light of appropriate wavelength at a site effected by the condition.

The present invention also provides for the use of zinc tri-(4-sulfobenzo)-5-mono-[(1-hexylcarboxy)naphtho]-porphyrazine for the treatment of a condition selected from the group consisting of a light accessible cancer, an ocular disease, extravasation and a leaky blood vessel and non-ocular vascular disease with light of appropriate wavelength.

Still in accordance with the present invention, there is provided the use of zinc tri-(4-sulfobenzo)-5-mono-[(1-hexylcarboxy)naphtho]-porphyrazine or a pharmaceutically acceptable salt thereof in the manufacture of a medicament to treat a condition selected from the group consisting of a light accessible cancer, an ocular disease, extravasation and a leaky blood vessel and non-ocular vascular disease in conjunction with light of appropriate wavelength.

Further still in accordance with the present invention, there is provided a method (and its use) of treating a condition selected from the group consisting of a light accessible cancer, an ocular disease, extravasation and a leaky blood vessel and non-ocular vascular disease in an individual comprising:
 a) administering an effective amount of zinc tri-(4-sulfobenzo)-5-mono-[(1-hexylcarboxy)naphtho]-porphyrazine or a pharmaceutically acceptable salt thereof; and
 b) irradiating the individual with light of appropriate wavelength at a site effected by the condition.

In a preferred embodiment of the invention, the ocular disease is preferably selected from the group consisting of age related macular degeneration, diabetic retinopathy, exudative retinal detachment, Coat's disease, haemangiomas, retinoblastomas, choroidal neovascularisation, diabetic microvasculopathy, clinically significant macular edema, edema associated with central retinal vein occlusion, edema associated with branch retinal vein occlusion, postoperative cystoids, intraocular inflammation, light toxicity, retinitis pigmentosa, drug induced macular edema.

The present invention can also be used to treat non-ocular vascular disease such as vascularised tumours or psoriasis.

The water-soluble, amphiphilic Pc-like structures of the present invention have numerous advantages over other photodynamic agents currently in clinic or clinical trial including their ease and high yield synthesis as single isomeric compounds, their ease of formulation in aqueous medium, their excellent photochemical properties resulting in high yield of cytotoxic reactive oxygen species (ROS), their red-shifted absorption maximum, where tissues are most transparent, and their multiple absorption maxima, allowing excitation at different wavelengths to modulate depth of treatment with therapeutic light.

BRIEF DESCRIPTION OF THE DRAWINGS

FIG. 8 illustrates a FACS analysis showing that EMBP-conjugated NVT-0275 is fully functional.

DETAILED DESCRIPTION OF THE PREFERRED EMBODIMENT

Figure 1:
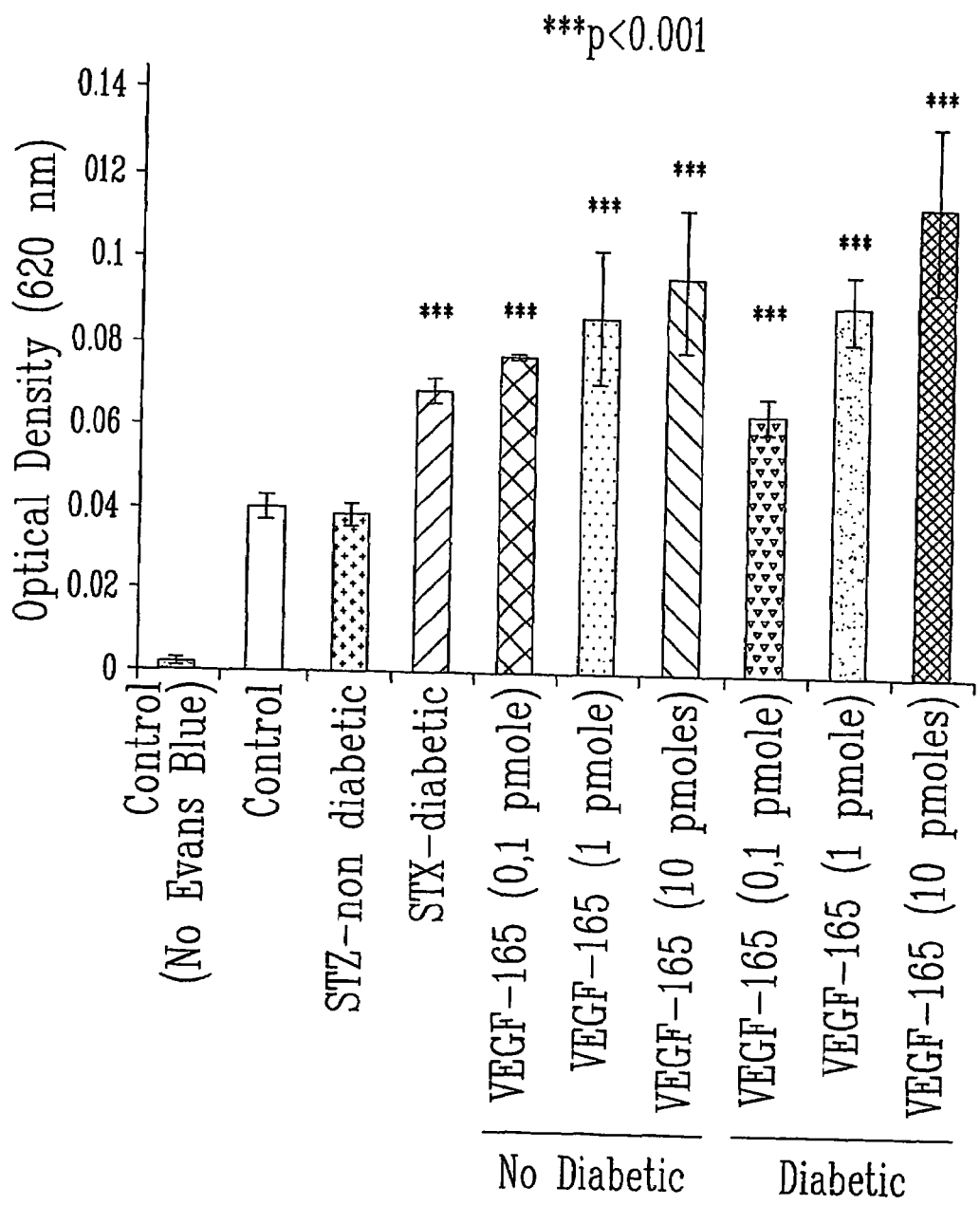
FIG. 1 shows a graph illustrating plasma extravasation produced by Vascular Endothelial Growth Factor in a rat model.

In a search of a water-soluble, amphiphilic Pc-like structures with multiple activation bands at red-shifted wavelengths (>680 nm), the inventors investigated the preparation of hybrid structures resembling both the basic Pc and naphthalocyane molecule, i.e. porphyrazines. In the present invention, it was thus found that tri-(sulfobenzo)-mono-(alkylyl-, aminoalkyl- or aminoaryl-naphtho)-porphyrazines (compounds 45-74 identified in the application) can be prepared as pure single products in good yield and that they exhibit excellent photodynamic properties against cancer cells in culture. By varying the length of the side chain of the alkylyl series (M=Zn) a parabolic relationship was found between the number of carbon atoms of the alkylyl chain and in vitro phototoxicity with the hexynyl derivative 46 exhibiting optimal photodynamic properties. The same derivative also showed excellent in vivo PDT response against an experimental mammary tumor in mice and strong capacity to shutdown the vasculature in the rat retina—an assay predictive of the potential use of a drug for the PDT of several retinopathies involving plasma extravasation including age-related macular degeneration (AMD) and diabetic retinopathy. These combined findings suggest that the hexynyl derivative 46 has excellent potential as a second-generation photosensitizing drug for the PDT of various medical conditions, particularly light-accessible cancers and retinopathies.

Coupling procedures for attachment of tri-(sulfobenzo)-mono-(carboxyl-naphtho)porphyrazines complexes to a protein carrier such as an antibody, preferably a monoclonal antibody (Mab) or its fragments involves commercially available reagents and published procedures to yield loading ratios of 7 up-to 15 moles of Pc per mole of Mab (N. Brasseur et al., Photochem. Photobiol. 69: 345-352, 1999; C. M. Allen, Photochem. Photobiol. 70: 512-523, 1999). At the lower loading ratios immuno integrity of the Mab is unaffected (M. Carcenac, et al., Photochem. Photobiol., 70: 930-936, 1999; M. Carcenac, et al., Br. J. Cancer, 85: 1787-1793, 2001). MAb can be selected to target the photosensitizers of the present invention to different medical conditions for immunophototherapy (i.e. different cancers, dry-form of AMD).

Chemistry

The general synthetic procedure for the preparation of compounds 45-74 implies adding lipophilic alkylyl, aminoalkyl or aminoaryl chains to the iodonaphtho moiety of the indole-protected key intermediate tri-(indolylsulfobenzo)-mono-(iodonaphtho)-porphyrazine (5-14). Varying the chain length of the peripheral alkylyl, aminoalkyl or aminoaryl substituent yields compounds 45-74 with graded amphiphilic properties.

The inventor's first attempt to prepare the key intermediate 5-14 involved the ring-enlargement reaction of a trichloro-sulfo subphthalocyanine (subPc). The success of the procedure depends dramatically on the nature of the substituents on the subPc, the reactivity of the iminoisoindoline used to open the ring structure to yield the 4-membered porphyrazine, the solvent and other factors, and the inventors discovered that this approach was not suitable for the preparation of iodonaphtho intermediates 5-14.

In a second approach to obtain the iodonaphtho intermediates 5-14 the mixed condensation reaction between iodo-2,3-dicyanonaphthalene (3-4) and the indole protected 3,4-dicyanophenylsulfonyl (2) in the presence of zinc acetate was successfully used. The resulting protected monoiodonaphtho compounds 5-14 are soluble in most polar organic solvents and can easily be purified by silica gel column chromatography. Their UV-vis spectra show a split Q band (725, 687 and 622 nm) due to the combined naphthalocyanine and phthalocyanine nature of the macrocycle, and the presence of the bulky protecting groups, which affect the symmetrical properties of the molecule. The protected iodonahpto-porphyrazines 5-14 (also referred to hereinbefore iodonaphtho intermediates) are highly versatile intermediates for the synthesis of novel mono(naphtho) substituted tri(sulfobenzo)-porphyrazines that are readily purified by column chromatography. Applying the palladium-catalyzed coupling of terminal alkynes with the iodonaphtho moiety provides an effective method for introducing an alkynyl chain onto the porphyrazine macrocycle, which upon hydrolysis yield compounds 45-74. Likewise, the palladium-catalyzed Buchwald amination reaction was employed to attach selected amino-chains onto the porphyrazine macrocycle providing analogs 45-74 substituted with various alkyl chains via an amino rather than an ethyne linkage.

All new porphyrazines were characterized by UV-vis and FAB (fast atom bombardment) or electron-spray mass spectroscopy. The trisulfonated porphyrazine compounds 45-74 were purified by reverse phase, medium pressure liquid chromatography and analysed by reverse phase HPLC. All derivatives showed three closely eluting peaks with longer retention times as compared to those of the parent molecule, i.e. a trisulfonated phthalocyanine. This observation confirms that the attachment of a lipophilic chain augments the hydrophobic properties of the trisulfonated porphyrazine compounds 45-74.

Scheme 1

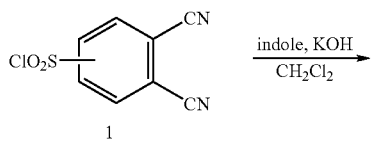

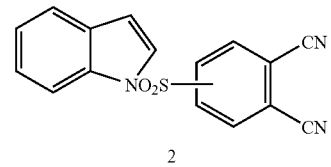

Scheme 2

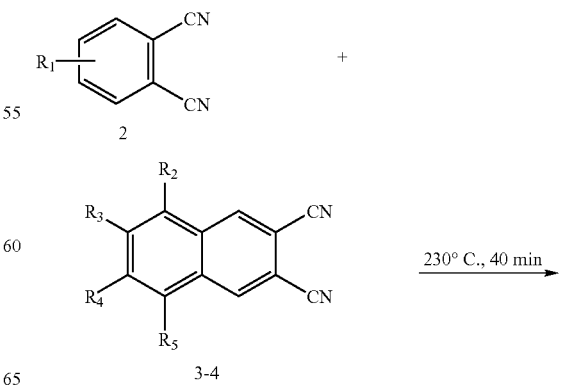

-continued

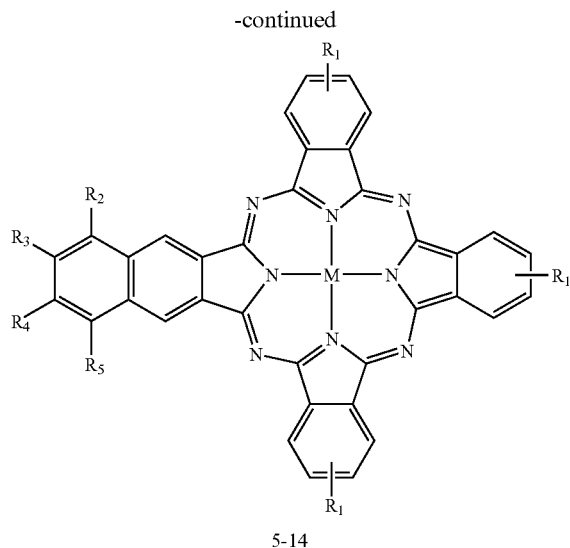

5-14

For 2, 5-14: $R_1$:
For 3, 5-9: $R_3, R_4, R_5 = H, R_2 = I$.
For 4, 10-14: $R_2, R_4, R_5 = H, R_3 = I$
For 5-14: (a) M = HH, (b) M = Zn, (c) M = Co(II), (d), M = Ni, (e) M = Cu.

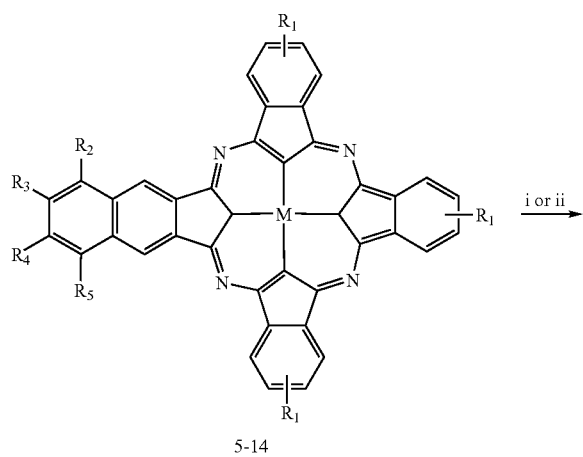

i or ii 5-14

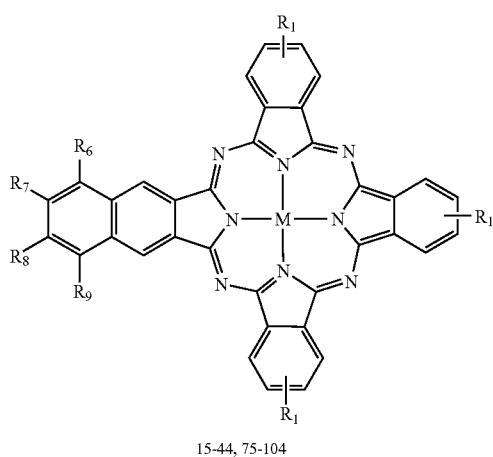

15-44, 75-104

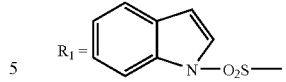

For 15-104: (a) M = HH, (b) M = Zn, (c) M = Co(II), (d), M = Ni, (e) M = Cu.
For 15-29, 75-79, 85-94: $R_7, R_8, R_9 = H, R_6 = $ -CCX or -NHX when X = alkyl, aryl, alkylcarboxyl or arylcarboxl.
For 30-44, 80-84, 95-104: $R_6, R_8, R_9 = H, R_7 = $ ——CCX or ——NHX when X = alkyl, aryl, alkylcarboxyl or arylcarboxyl.

i. for 15-19, 30-34, 75-84: PdCl$_2$(Ph$_3$P)$_2$/CuI/THF/1-alkyne or alkynecarboxyl.
ii. for 20-29, 35-44, 85-104: Pd$_2$(dba)$_3$/BINAP/CsCO$_3$/THF, alkylamine, arylamine, carboxyllalkylamine or carboxylarylamine.

Scheme 4

15-44, 75-104 $\xrightarrow{\text{NaOMe/THF/MeOH}}$

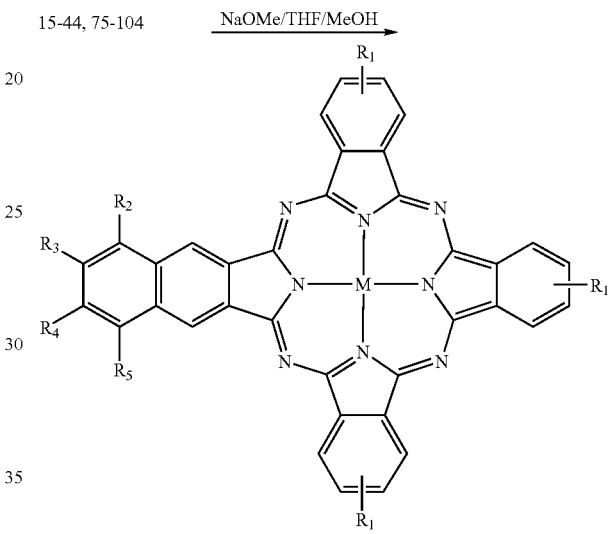

45-74, 105-114

For 45-74, 105-114: $R_1 = SO_3^-Na^+$.
For 45-74, 105-114: (a) M = HH, (b) M = Zn, (c) M = Co (II), (d), M = Ni, (e) M = Cu.
For 45-59, 105-109: $R_3, R_4, R_5 = H, R_2 = $ ——CCX or ——NHX when X = alkyl, aryl, alkylcarboxyl, or arylcarboxyl.
For 60-74, 110-114: $R_2, R_4, R_5 = H, R_3 = $ ——CCX or ——NHX when X = alkyl, aryl, alkylcarboxyl, arylcarboxyl.

Biology

Formulation of Trisulfonated Porphyrazines

A few milligrams of the selected tri-(4-sulfobenzo)-5-mono-[(1-alkylyl)naphthalo]-porphyrazines (Scheme 4: compounds 45-74) were dissolved in 1% PBS (pH 7.4) and sonicated for a few minutes. The solutions were filtered on Millex-GV™ 0.22 μM (Millipore) under sterile condition. The final concentration of the dyes was determined by their UV-vis absorption after dilution in methanol ($\lambda_{max}$ 680-690 nm, $\epsilon = 1.20 \times 10^5$ M$^{-1}$cm$^{-1}$).

Phototoxicity Against Tumor Cells in Culture

Cell Culture

EMT-6 murine mammary tumor cells were maintained in Waymouth medium culture (Gibco, Burlington, Canada) supplemented with 15% fetal bovine serum (Gibco), 1% glutamine (Gibco) and 1% penicillin-streptomycin (Gibco). This corresponded to a complete medium.

Cellular Photoinactivation

Cell cultures were trypsinated to give a $1.5 \times 10^5$ cells/ml suspension. 100 μL of cells per well were plated in 96 multi-well plates and incubated overnight at 37° C., 5% $CO_2$. One column of cells were omitted to serve as a blank. The cells were rinsed twice with PBS and incubated with 50 μL of dye solution (1-5 μM) in Waymouth 1% FBS for 1 or 24 h. One control column was filled with dye-free Waymouth 1% FBS. The cells were then rinsed twice with PBS, re-fed with 100 μL of Waymouth 15% FBS and exposed for varying time intervals to red light (10 mW $cm^{-2}$ at 660-700 nm). Plates were incubated overnight at 37° C., 5% $CO_2$. Cell survival was measured by a colorimetric method, using the tetrazolium salt 3-(4,5-dimethylthiazol-2-yl)-2,5-diphenyl-tetrazolium bromide (MTT) (Sigma). Eight-fold replicates were run and experiments were repeated at least three times.

MTT Assay

A stock solution of MTT at 0.5% in PBS was prepared and kept at 4° C. in the dark. The solution was diluted 5-fold in Waymouth 15% FBS and 50 μL was added in each well. After 4 h incubation (37° C., 5% $CO_2$), 100 μL sodium dodecyl sulfate (10% in 0.01 N HCl), was added in the wells to stop MTT reduction and to dissolve the blue formazan crystals produced by mitochondrial hydrogenases in living cells. After 24 h incubation, the plates were read on a microplate reader (molecular devices, thermomax) to the optical densities at 570 nm. The survival curves were plotted as a function of light dose and $LD_{90}$ values were calculated.

Efficacy of PDT for the In Vivo Treatment of Tumors

Animal Model

All experiments were performed on male BALB/c mice (18-22g) (Charles River Breeding Laboratories, Montreal, Quebec, Canada) bearing two EMT-6 mammary tumours. The experiments were conducted following a protocol approved by the Canadian Council on Animal Care and the in-house ethics committee. Animals were allowed free access to water and food throughout the experiments. Before tumour implantation, hair on the hind legs and the backs of the mice was removed by shaving and chemical depilating (Nair, Whitehall, Mississauga, Canada). The two tumors were implanted on the backs of the animals by intradermal injection of $2-3 \times 10^5$ EMT-6 cells suspended in 0.05 ml Waymouth's growth medium.

Photodynamic Therapy (PDT)

For PDT tumor response studies, mice were used 7-10 d after tumor cell inoculation (mean external tumor size 4.5-6.0 mm diameter and approximately 2.5 mm thickness). The mice were given an intravenous administration of 1 μmol of porphyrazine dye in PBS (0.2 mL/20 g) through the tail vein. After 24 h, one tumor was treated with an 8-mm beam of red light (670 nm, 200 mW/$cm^2$ for a total fluorence of 400 J/$cm^2$, generated by a B&W fibre-coupled diode laser, model BWF-670-3000, B&W Tek, Newark, Del.) whereas the other tumour served as a control. Mice were examined daily for 20 days following PDT in order to assess tumor response (necrosis) and recurrence.

Efficacy of PDT for the Treatment of Retinopathies

Experimental Diabetes

Plasma Extravasation as a Measure of Retinopathy

The long established Evans Blue technique was used to measure plasma extravasation. Under anesthesia with a 10 mg/kg mixture of Ketamine and Xylazine, 250 g male wistar rats were injected with 45 mg/kg Evans Blue through a canula placed in the jugular vein. Ten minutes later, the experimental procedure was started. At the end of experiments, the animals were sacrificed and their eyes were enucleated. Both eyes combined were placed into 300 μl of formamide and incubated at 70° C. for 18 hours. Following incubation the supernatant absorbance at 620 nm was read with a spectrophotometer. A standard curve was used to determine the concentration of Evans Blue, which was expressed in μg/ml.

Induction of Plasma Extravasation Using Vascular Endothelial Growth Factor (VEGF-165, Vascular Permeability Factor)

Rats anesthetized with a mixture of Ketamine and Zylazine (10 mg/kg) were injected with 2 μl of VEGF-165 prepared in saline, directly into the vitreous, using a Hamilton micro syringe. A period of 10 min was allotted for the plasma extravasation response to occur. After the response to VEGF-165 developed, the eyes were enucleated and subjected to spectrophotometric analysis for Evan's Blue.

Plasma Extravasation in the Diabetic Rat

After an overnight fast, diabetes was induced with a single 65 mg/kg intraperitoneal injection of streptozotocin (STZ) in 10 mM citrate buffer, pH 4.5. Animals that served as non diabetic controls received an equivalent amount of citrate buffer alone. One week later, just prior to experimentation, blood glucose levels were measured to determine diabetic status. Only rats with blood glucose higher than 20 mM were deemed STZ-diabetic. Those rats that were injected with STZ but did not become diabetic were deemed STZ-non diabetic controls.

Photodynamic Treatment with Trisulfonated Porphyrazines

Conscious rats were injected with the photosensitizing drug through the tail vein six hours prior to irradiation with red light onto the retina. The light was applied continuously for 15 min using a laser pen and circular motion to ensure that the entire retina was uniformly illuminated ($\lambda$=680 nM; 50 mW/$cm^2$; 45 J/$cm^2$). Subsequently the eyes were enucleated and tested for Evan's Blue levels.

Isolation of Polymorphonuclear Leukocytes

Dextran 3% is equilibrated to room temperature (72° C.) and then thoroughly mix blood 1:1 (v:v). The mixture is allowed to decant for 35 min at room temperature. Ten (10) ml of Ficoll is put in a 50 ml tube and then the supernatant is aspirated from the blood cells and delicately add to the Ficoll in the tube, which is then centrifuged for 30 min at 2000 rpm, at room temperature and without brakes. Once the centrifuge has stopped, the upper layer containing the plasma is collected. The layer of monoleukocytes is put in a 15 ml tube. α-MEM-C is then added to these cells. The pellet (PMN+RBC) is resuspended in 2 ml of NaCl 0.2% for 25 sec. Then two (2) ml of NaCl 1.6% and 6 ml PBS are added. The suspension is then centrifuged for 10 min at 1300 rpm at room temperature and the supernatant removed. The new pellet (PMN and RBC) is resuspended again in 2 ml of NaCl 0.2% for 25 secand then two (2) ml of NaCl 1.6% and 6 ml of PBS are added. the suspension is once again centrifuged for 10 min at 1300 rpm at room temperature and the supernatant removed. α-MEM-C is then added to resuspend the pellet to make a cell suspension. The cellular concentration is then adjusted to $3 \times 10^6$ cells/ml. Nine hundred (900) μl of cells are poured into 24-well plates. NVT-0275-Ab is then added and let to sit for 1 hour in dark. The wells are then exposed to red light (8-mm beam, 670 nm, 200 mW/$cm^2$, generated by a B&W fibre-coupled diode laser, model BWF-670-3000, B&W Tek, Newark, Del.) during a period of 5 min, i.e. 0.2 min per well (for a total fluence of 2 J/cm$^2$). Finally, the cells are collected in a tube and FACS is conducted.

FACS was conducted according to standard procedures (see for example Bortner C. D. and J. A. Cidlowski, Flow Cytometric Analysis of Cell Shrinkage and Monovalent Ions during Apoptosis, In: Apoptosis (vol 66), Methods in Cell Biology, Edited by L. M. Schwartz and J. D. Ashwell, Academic Press, 2001).

The present invention will be more readily understood by referring to the following examples, which are given to illustrate the invention rather than to limit its scope.

EXAMPLE 1

1-(3,4-Dicyanophenylsulfonyl)indole 2 (Scheme 1)

Ground KOH (8.6 g) was mixed with tetrabutylamonium hydrogen sulfate (830 mg) in CH$_2$Cl$_2$ (230 mL). The reaction flask was cooled in an ice-salt bath (~-5° C.). After stirring about 10 min, indole (9.04 g) was added in the mixture. The reaction mixture was allowed to stir for 20 min in the cooling bath. The compound 1, sulfonyl chloride powder was added to the reaction mixture over 50 min at 0° C. ~-5° C., and the solution was continuously stirred for about 4 h at room temperature (the reaction was monitored by TLC, and continued until the starting material was gone). The solid KOH was removed by filtration and the filtrate was diluted with CH$_2$Cl$_2$ to 600 ml, washed with 10% aqueous HCl, water, saturated NaHCO$_3$ aqueous solution and water (Caution: All the washing must use the cooling solution). The solvent was removed under vacuum. The residue was dispersed in 150 mL CH$_2$Cl$_2$ under sonication, filtered and the filtrate was absorbed on silica gel and compound 2 was eluted with hexane/EtOAc (100/5 ~ 100/40) and recovered as a light yellow powder (8.94 g, 62.4%). Compound 2 had the following characteristics:

m.p.:171~173° C.;MS(M$^+$):307.

EXAMPLE 2

Zinc tri-[4-(1-indolylsulfobenzo)]-mono-5-iodonaphtho porphyrazine (6) (Scheme 2)

A mixture of compound 2 (300 mg, 0.97 mmol), compound 3 (100 mg, 0.32 mmol) and ZnAc.2H$_2$O (200 mg, 0.91 mmol) was heated to 210° C. ~230° C., and kept at this temperature for 40 min, then cooled to room temperature. The crude product was dissolved in THF, filtered to remove solids and evaporated under reduced pressure. The residue containing the crude product was dissolved in CHCl$_3$. The purification was carried out by silica gel column chromatography in toluene/THF (100/1~100/5) to afford compound 6 (74 mg, 18.5%) with the following characteristics:

MS(FAB, M$^+$):1289;UV-vis,$\lambda_{max}$in nm($\epsilon$ in M$^{-1}$ cm$^{-1}$):725(1.05×10$^5$),687(1.20×10$^5$),622(3.82× 10$^4$),349(6.75×10$^4$).

EXAMPLE 3

Zinc tri-[4-(1-indolylsulfobenzo)]-5-mono-[(1-hexynyl)naphtho]-porphyrazine (16) (Scheme 3)

Compound 6 (119 mg, 0.09 mmol), PdCl$_2$(PPh$_3$)$_2$ (25 mg) and CuI (25 mg) were placed in a two neck-flask under nitrogen. Anhydrous THF (8 ml) was added into the flask by syringe. Nitrogen was bubbled through the mixture, 1-hexyne (0.2 mL) and Et$_3$N (5 mL) were added by syringe, respectively. Nitrogen continued to pass through the reaction mixture for 10 min. Then the reaction mixture was stirred for an additional 20 h at room temperature. The solvent was removed under reduced pressure. The residue was dissolved in CHCl$_3$, purified by column chromatography in Toluene/THF (100/1 to 100/10) to yield 16 as a green powder (99 mg, yield: 84%) having the following characteristics:

MS(FAB, M$^+$):1245;UV-vis,$\lambda_{max}$in nm ($\epsilon$ in M$^{-1}$ cm$^{-1}$):725(1.03×10$^5$)687(1.18×10$^5$),622(3.80× 10$^4$),349(6.72×10$^4$).

EXAMPLE 4

Zinc tri-[4-(1-indolylsulfobenzo)]-5-mono-[(1-hexylamino)]-porphyrazine (21) (Scheme 3)

A mixture of cesium carbonate (50 mg, 0.15 mmol), Pd$_2$(dba)$_3$ (5 mg) and (s)BINAP (5 mg) was placed in a two neck round flask, and purged with N$_2$. Compound 6 (40 mg, 0.03 mmol) was added and anhydrous THF (7 mL) and hexylamine were then added by syringe. The reaction mixture was heated to reflux under nitrogen and kept refluxing for 19 h (the reaction was monitored by TLC), then cooled to room temperature. The solvent was evaporated on a vacuum. The residue was dissolved in CHCl$_3$, then separated by column chromatography in toluene/THF (100/5), the first band was identified as compound 21 (25 mg, yield: 63%). MS (FAB: M$^+$), 1262.

EXAMPLE 5

Zinc tri-(4-indolysulfobenzo)-5-mono-[(1-hexylcarboxy)naphtho]-porphyrazine (76) (Scheme 3)

Compound 6 (87 mg), PdCl$_2$(PPh$_3$)$_2$ (25 mg), CuI (50 mg) and 5-hexynoic acid (2 ml) were placed in the two neck-flask, and the flask was fleshed by nitrogen. Anhydrous THF (4 ml) was added into the flask by syringe. Nitrogen was bubbled through the mixture. Et$_3$N (4 ml) were added by syringe while the mixture was kept under nitrogen. After the reaction mixture was stirred for 24 h at room temperature the solvent was removed under reduced pressure. The residue was dissolved in the CHCl$_3$ and purified by column chromatography in CHCl$_3$/MeOH/AcOH (1:1:0.2), to afford 76 as a green powder (74 mg, yield: 82%).

MS(FAB,M$^+$):1223.

EXAMPLE 6

Zinc tri-(4-sulfobenzo)-5-mono-[(1-hexynyl)naphtho]-porphyrazine (46) (Scheme 4)

A solution of NaOMe (120 mg, metal sodium was dissolved in 10 mL methanol) was added to a solution of compound 16 in 15 mL THF. The mixture was refluxed for 24 h. The solvent was removed in a vacuum, the residue was washed with acetone to remove soluble organic impurities. The residue was dried in air. The crude product was dissolved in buffer solution (pH=5), and the pH value of the solution was adjusted to 7. The purification was carried out on C-18 reverse phase column (via vacuum) to remove salt. The column washed with aqueous phosphate buffer (pH=5) and water to elute the salt, and 50% methanol/water to elute pure compound 46 (74 mg, 91.6%) with the following characteristics:

MS[electrospray,ZnNPcC$_6$(SO$_3$H)$_3$]:947.9.UV-vis, $\lambda_{max}$ in nm ($\epsilon$ in M$^{-1}$cm$^{-1}$): 703(1.12×10$^5$),680 (1.21×10$^5$),648(3.46×10$^4$),617(2.86×10$^4$),339 (3.73×10$^4$).

EXAMPLE 7

Zinc tri-(4-sulfobenzo)-5-mono-[(1-hexylamino) naphtho]-porphyrazine (51) (Scheme 4)

A solution of NaOMe (50 mg, metal sodium was dissolved in 5 mL methanol) was added to a solution of compound 20 (25 mg, 0.02 mmol) in 10 mL THF. The mixture was refluxed for 24 h, then cooled to room temperature. The solvent was removed on a vacuum, the residue was washed with acetone to remove soluble organic impurities. The precipitate was dried in the air. The crude product was dissolved in buffer (pH=5), and the pH value of the solution was adjusted to 7. The purification was carried out on a C-18 reverse phase column (via vacuum) to remove salt. The column washed with pH=5 phosphate buffer and water to elute the salt, and then with 50% methanol/water to elute pure compound 11 (15 mg, 73%) with the following characteristics:

MS[electrospray,ZnNPcC$_6$N(SO$_3$H)$_3$]:965.

EXAMPLE 8

Zinc tri-(4-sulfobenzo)-5-mono-[(1-hexylcarboxy) naphtho]-porphyrazine (106) (Scheme IV)

A solution of 76 (70 mg) in THF (8 ml) was added to a NaOMe solution in MeOH (72 mg Na was dissolved in 8 ml MeOH). The mixture was refluxed for 24 h. The solvent was removed under reduced pressure, the residue was washed with acetone to remove soluble organic impurities. The crude product (residue) was air-dried, dissolved in buffer solution (pH=5), and the pH of the solution was adjusted to 7. The purification was carried out on a C-18 reversed-phase column to remove salt. The column was than washed with pH=5 aqueous buffer (NaH$_2$PO$_3$), than water to elute the salt, and subsequently with 50% methanol/water to elute pure compound 106 (48 mg, 82%).

MS[electrospray,ZnNPcC$_6$(SO$_3$H)$_3$COOH]:925.

EXAMPLE 9

Phototoxicity of Trisulfoporphyrazines 45-49 Against EMT-6 Tumor Cells In Vitro

No dark toxicity was observed with any of the dyes under study up to 100 μM during a 24-h incubation period in Waymouth 1% FBS. The EMT-6 cells were incubated at 37° C., 5% CO$_2$ with dyes at 1 μM for different time intervals from 1 h to 24 h. The cell survival was plotted against the fluence (J.cm-2) to give survival curves for each compound tested and for each incubation time. From these curves the amount of light for 90% cell kill (LD$_{90}$) was interpolated as a quantitative measure of relative photocytotoxicity.

The LD$_{90}$ values of compounds 45-49 and the parent zinc trisulfophthalocyanine (ZnPcS$_3$) for the 6 h and 24 h incubation times are summarized in Table 1. The table reveals a parabolic relationship between the length of the alkylyl substituent (n=number of C-atoms) in the zinc tri-(4-sulfobenzo)-5-mono-[(1-alkylyl)naphtho]-porphyrazine (Scheme 4, compounds 45-49) and their phototoxicity, with the 1-hexynyl derivative 46 (n=6) exhibiting the highest phototoxicity followed by the 1-ethynyl derivative 45 (n=2) and the 1-nonyne derivative 47 (n=9). Further increase in the length of the 1-alkylyl side chain (compounds 48 and 49, n=12 and n=16, respectively) leads to substantial decrease in the photodynamic potential of the dyes. The parent ZnPcS$_3$, lacking both a side chain (n=0) and a benzyl group, was less active than all three porphyrazine derivatives 45, 46 and 47 after 6 h incubation. After 24 h incubation the ZnPcS$_3$ showed higher phototoxicity than 47 but remained less active than 45 and 46.

TABLE 1

LD$_{90}$ in J · cm$^{-2}$ of a series of trisulfonated porphyrazines 45-49 with alkylyl substituents varying from 2-16 carbon atoms (n)

| Incubation time (hours) | LD$_{90}$ (J · cm$^{-2}$) | | | | | |
|---|---|---|---|---|---|---|
| | 45 (n = 2) | 46 (n = 6) | 47 (n = 9) | 48 (n = 12) | 49 (n = 16) | ZnPcS$_3$ (n = 0) |
| 6 | 5.1 | 4.1 | 4.9 | >12 | >12 | 5.9 |
| 24 | 1.8 | 1.2 | 4.5 | 9.2 | >12 | 2.2 |

EXAMPLE 10

PDT with Trisulfoporphyrazine 46 to Treat Solid Mammary Tumors in a Mouse Model

Photodynamic Treatment with Trisulfoporphyrazine 46 of Mouse Tumors

The compound most active in the in vitro tumor cell assay, i.e. the trisulfoporphyrazine 46, was further tested for its photodynamic potency in an in vivo mouse tumor model using the EMT-6 cell line. The results are summarised in Table 2. Mice that received vehicle only (PBS) did not show any tumor response, nor did the control tumors that were shielded from light. All treated tumors responded within 48 h after PDT (flattening and necrosis) at all dye doses used, i.e. 0.5-1 μmole/kg. At the highest dye dose over 50% of the animals responded with complete tumor regression as observed 3 weeks after treatment. No mortality occurred at any of the dye and light doses used in the study.

TABLE 2

Gross tissue effects following PDT with compound 46 on EMT-6 tumors in Balb-c mice

| Dye | Dye dose (μmole/kg) | Mice (n) | Necrosis[1] (%) | Cure[2] (%) | Mortality (%) |
|---|---|---|---|---|---|
| 46 | 1 | 13 | 100 | 54 | 0 |
| 46 | 0.75 | 5 | 100 | 20 | 0 |
| 46 | 0.5 | 5 | 100 | 0 | 0 |
| PBS | control | 4 | 0 | 0 | 0 |

[1]Necrosis is identified as the appearance of flat and necrotic tissue within 2 days post-PDT as observed macroscopically.
[2]Cure is defined as the absence of a palpable tumor 3 weeks post-PDT

EXAMPLE 11

PDT with Trisulfoporphyrazines 45-47 to Treat Extravasation in Rat Retinopathy Models Vascular Endothelial Growth Factor (VEGF-165) Injected Rat Model Administration of 0.1, 1, and 10 pmoles VEGF-165 (Vascular Endothelial Growth Factor, Vascular Permeability Factor) produced a dose dependent increase of plasma extravasation in both non-diabetic and in STZ-diabetic Wistar rats (FIG. 1).

Figure 2:
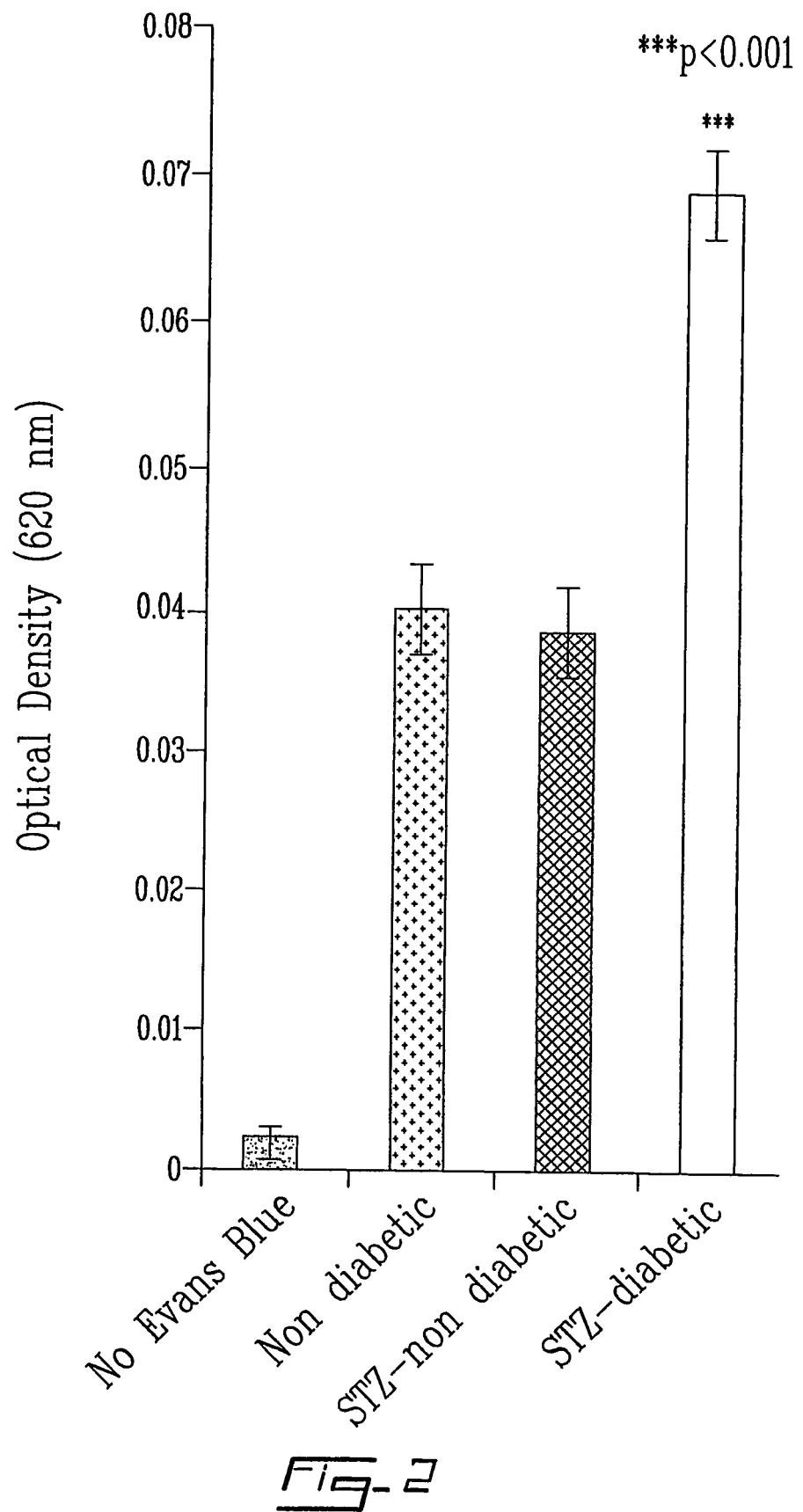
FIG. 2 shows elevated plasma extravasation resulting from diabetes in the streptozotocin (STZ)-injected rat model.

In a group of rats, a series of control experiments were conducted to ensure the validity of the experimental design (FIG. 2). Formamide extracts from eyes taken from control Wistar rats that were not injected with Evan's Blue showed near zero absorbance at 620 nm (O.D.<0.005). Control Wistar rats injected with Evan's Blue (45 mg/kg, i.v.) but not with VEGF-165 showed a low level of absorbance at 620 nm (O.D.=0.04). The low level of absorbance found in control Wistar rats corresponds to the amount of Evan's Blue trapped in the blood vessels at the time of sacrifice. The amount measured in STZ-non diabetic rats (blood glucose<20 mM) was not significantly different from the control (i.e. O.D.=0.04), demonstrating that any increase in plasma extravasation observed in STZ-diabetic rats, is due to diabetes and not to a possibly acute toxic effect of the STZ drug. STZ-diabetic rats (blood glucose>20 mM) treated with 65 mg/kg of streptozotocin had significantly increased Evan's Blue in the retina (FIG. 2).

Photodynamic Treatment of Leaking Vessels in the Rat Retina with Trisulfoporphyrazine 46

Figure 3:
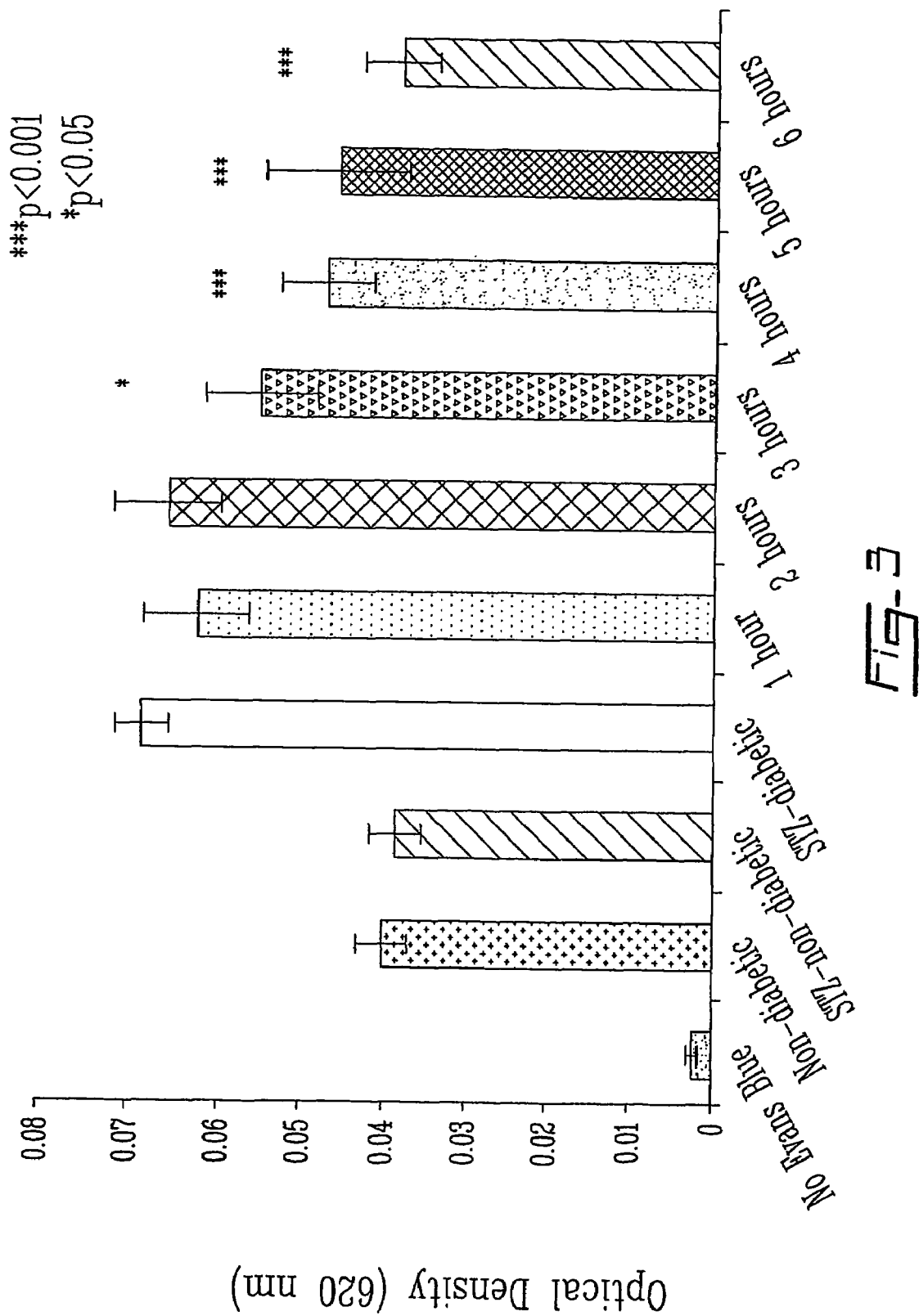
FIG. 3 illustrates a time-dependent inhibition of Vascular Endothelial Growth Factor evoked plasma extravasation.
Figure 4:
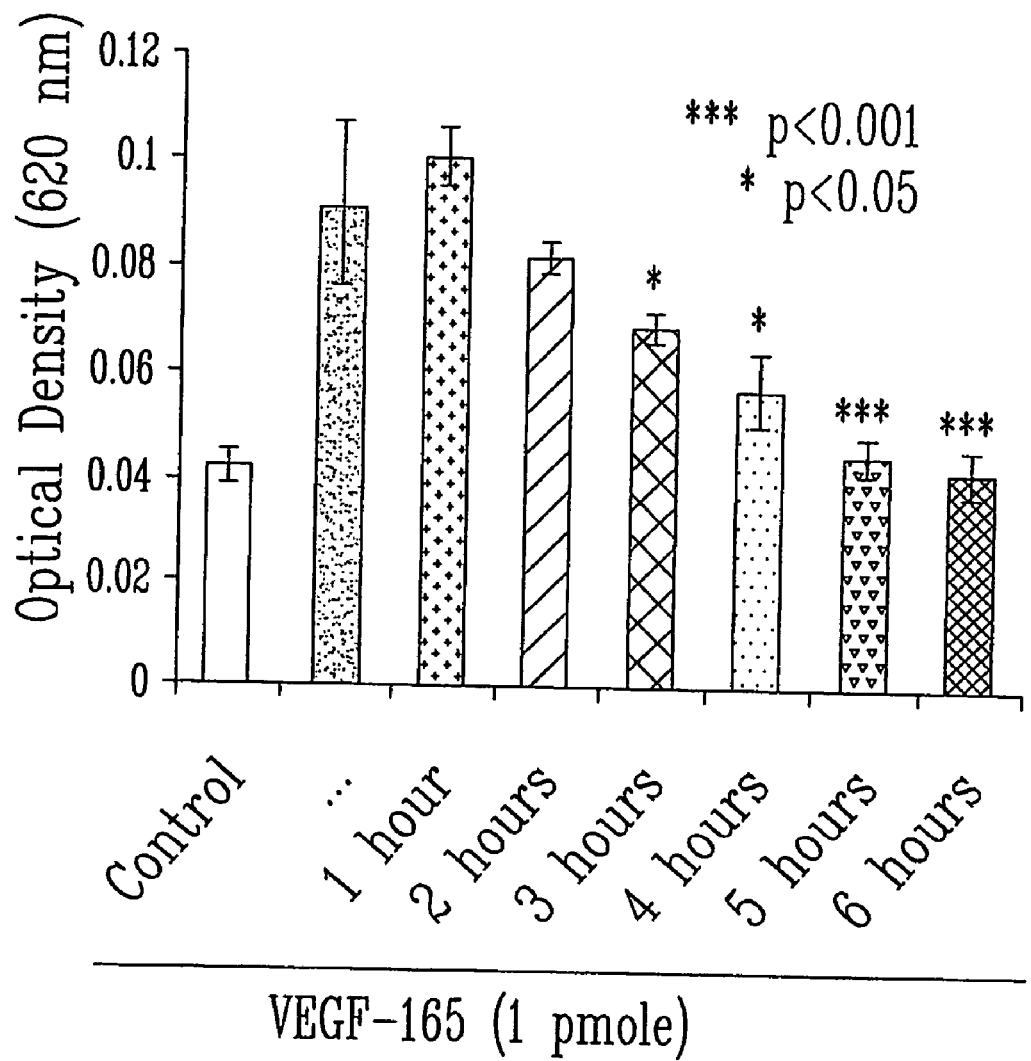
FIG. 4 illustrates a time-dependent inhibition of plasma extravasation in STZ-diabetic rat retinal vessels.

The PDT response was shown to be dependent on the time interval between photosensitizer administration and red light application (FIGS. 3 and 4). In VEGF-165 treated STZ-diabetic rats plasma extravasation reach control levels after a 5 hour interval between photosensitizer administration and light application (FIG. 3). PDT with 46 in STZ-diabetic rats reduced plasma extravasation to the level of control non-diabetic rats when this period was extended from 1 hour up to 6 hours (FIG. 4).

Structure-Activity Relationships in PDT Efficacy to Reduce Plasma Extravasation

Figure 5:
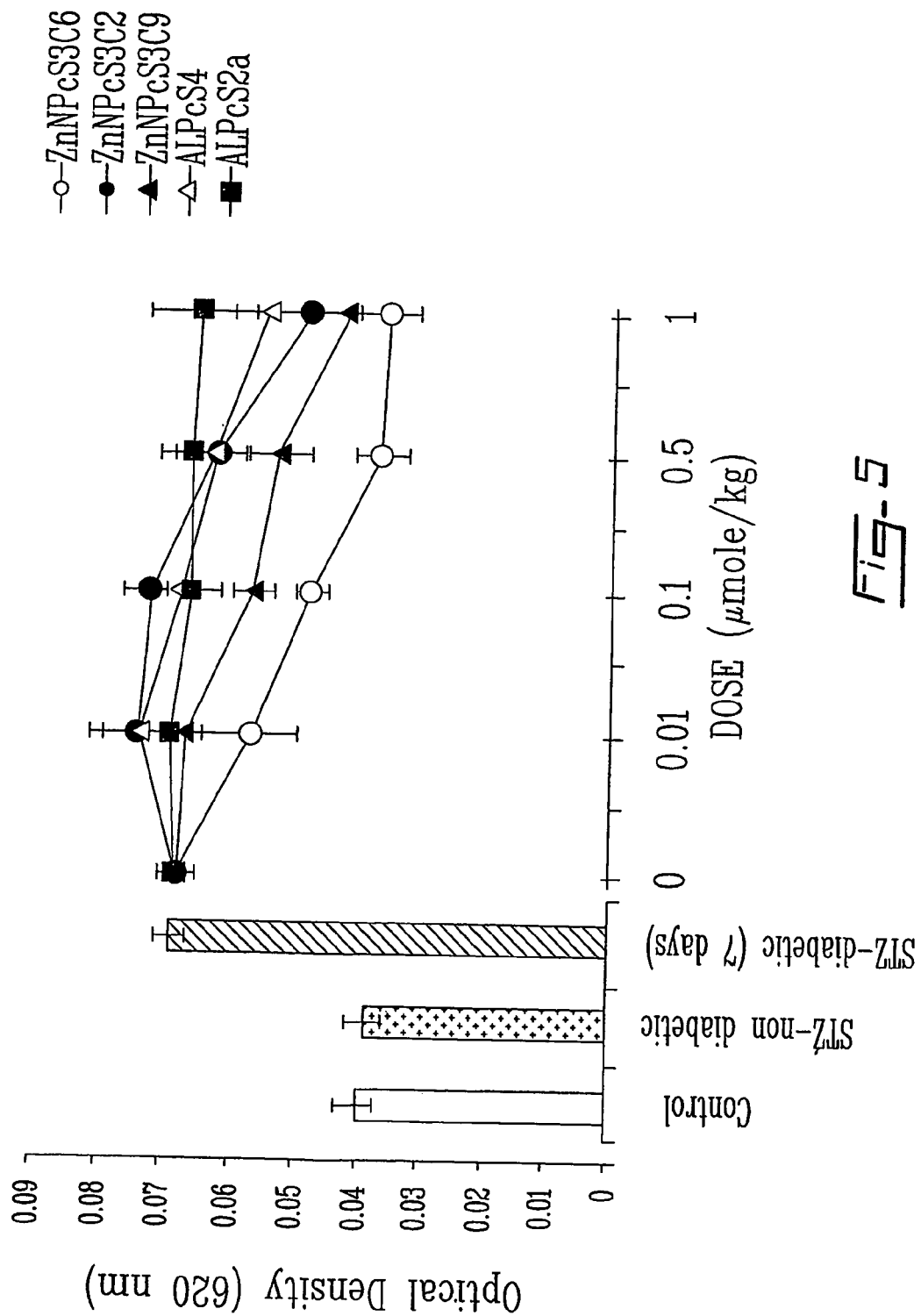
FIG. 5 illustrates dose response curves of various compounds of the present invention using an optimal PDT protocol (i.e. red light is applied 6 h after drug administration)

Using the optimal PDT protocol (i.e. 6 h after drug administration red light is applied), dose response curves were produced for ZnNPcS$_3$C$_6$ (46) and four analogs including ZnNPcS$_3$C$_9$ (47, with extended aliphatic side chain), ZnNPcS$_3$C$_2$ (45, with shortened aliphatic side chain), a phthalocyanine analog featuring an additional sulfate group instead of an aliphatic side chain, i.e. AlPcS$_4$ and the amphiphilic disulfonated reference phthalocyanine AlPcS$_{2a}$ (FIG. 5). All compounds produced a dose dependent inhibition of plasma extravasation. Of the five molecules that were tested, compound ZnNPcS$_3$C$_6$ (46) was the most potent inhibitor of plasma extravasation. At 0.5 μmole/kg compound 46 completely inhibited plasma extravasation in the STZ-diabetic rat after exposure of the retina (about 7 mm²) to a relative low dose of red light (45 J/cm2, total fluence 3 J). None of the other dyes tested were able to induce complete inhibition of extravasation even at the highest test dose of 1 μmole/kg (FIG. 5).

To summarize, in the VEGF-165 injected rats and the diabetic rats, both models of retinopathy, a 0.5 μmole/kg dose of ZnNPcS3C6 (46) combined with low level (680 nm; 25 mW/cm²; 20 J/cm²) red light application, completely inhibited plasma extravasation to control levels.

EXAMPLE 12

Targeted Photoinactivation of Human Polymorphonuclear Leukocytes with a MAb-Pophyrazine Conjugate (EMBP-106)

Antibody-Porphyrazine Conjugate Preparation (EMBP-106)

The goal was to target 106 (also referred to herein as NVT-0275) to WBCs using antibodies. Hereinafter it is demonstrated using NVT-0275 conjugated to a non-specific protein (albumin) and in other experiments to an antibody specific for eosinophiles (EMBP) that the photosensitizer of the present invention remains highly functional, allowing thus to target specific cells with functional NVT-0275 conjugated to the antibody.

The monocarboxy compound 106 (ZnNPcS$_3$C$_6$—COOH) was coupled to a MAb raised against Eosinophil Major Basic Protein (EMBP, Azide free, United States Biological Co., Swampscott, Me., USA) by the carbodiimide method as described in the literature (N. Brasseur et al., *Photochem. Photobiol* 69: 345-352, 1999; and M. Carcenac et al., *Photochem. Photobiol,* 70: 930-936, 1999). Briefly, the monocarboxy group of 106 (0.8 μmole) was activated with 1-(3-dimethylaminopropyl)-3-ethyl-carbodiimide hydrochloride (3 μmole) (EDAC, Aldrich) and N-hydroxysulfosuccinimide (1.5 μmole) (NHSS, Pierce). The activated 106 was purified on a C-16 SetPak (Waters), eluted with MeOH and evaporated to dryness. EMBP (0.1 mg) in 1 ml phosphate buffer pH 8 was added and the mixture was agitated for 12 h at 4 C, purified over a Sephadex G-50™ column in phosphate buffer and concentrated by centrifugation (Centricon™). The final concentration of the EMBP-bound 106 was estimated by its absorbance at 340 nm ($\epsilon=80\times10^3$ M$^{-1}$ cm$^{-1}$). The final EMBP-106 preparation contained 8 mole 106 per mole of EMBP. The same procedure was followed to couple 106 to a non-specific protein (albumin) giving similar dye loading yields of 8-10 mole 106 per mole of protein.

Figure 6A:
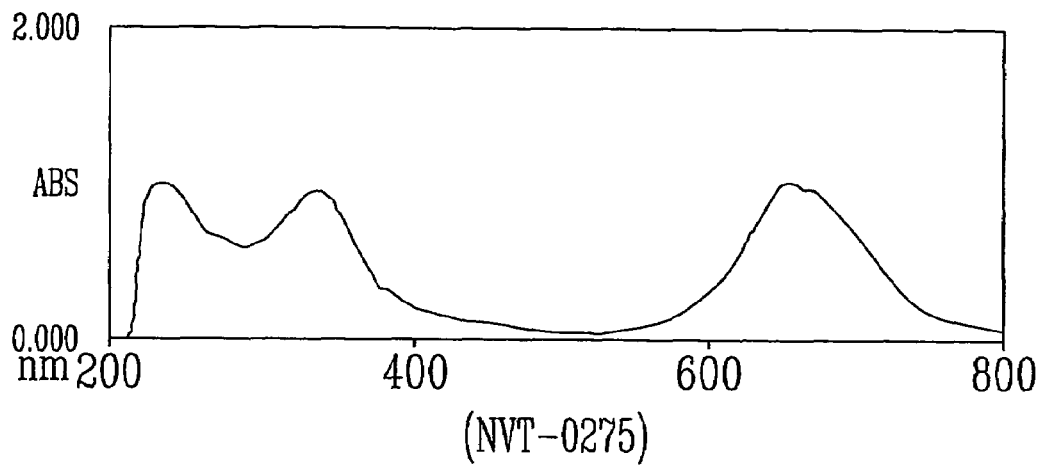
FIGS. 6A and 6B illustrate the absorption spectrums of NVT-0275 (compound 106) and of NVT-0275 conjugated to albunim.
Figure 6B:
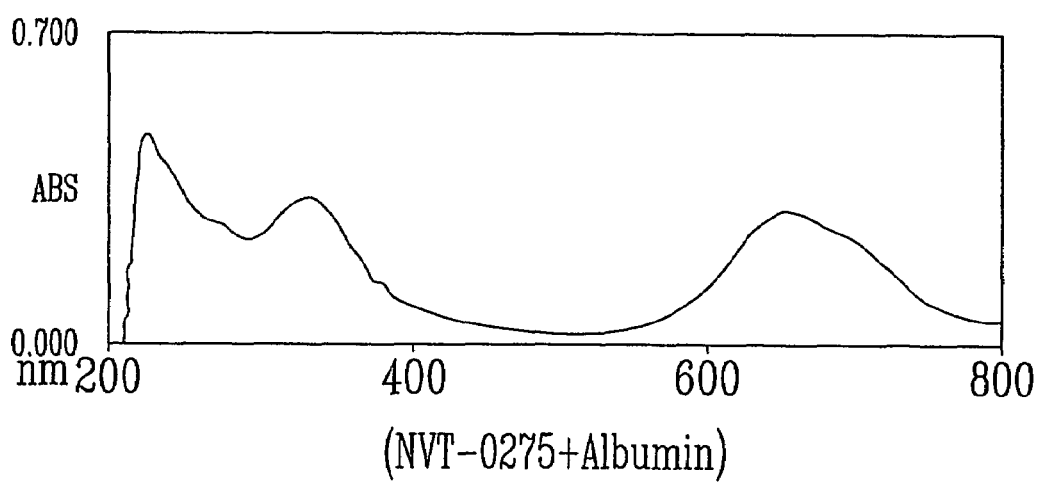

In FIGS. 6A and 6B, it is demonstrated that the triple absorption peaks of NVT-0275 are maintained after conjugation with protein (albumin). FIG. 6A shows the spectrum of NVT-0275 with its characteristic triple absorbance peaks. FIG. 6B shows the spectrum of albumin conjugated NVT-0275. The absorbance pattern has not been changed by conjugation with the protein.

To access the targeting of the NVT-0275 to white blood cells, only blood from a healthy donor whom naturally has a high eosinophile count were used. The blood had about 5000 eosinophiles/μl which equates to about 50% of the white blood cells (WBCs). Eosinophiles usually account for 2-4% of peoples WBC count. WBCs were isolated using standard procedures.

Figure 7:
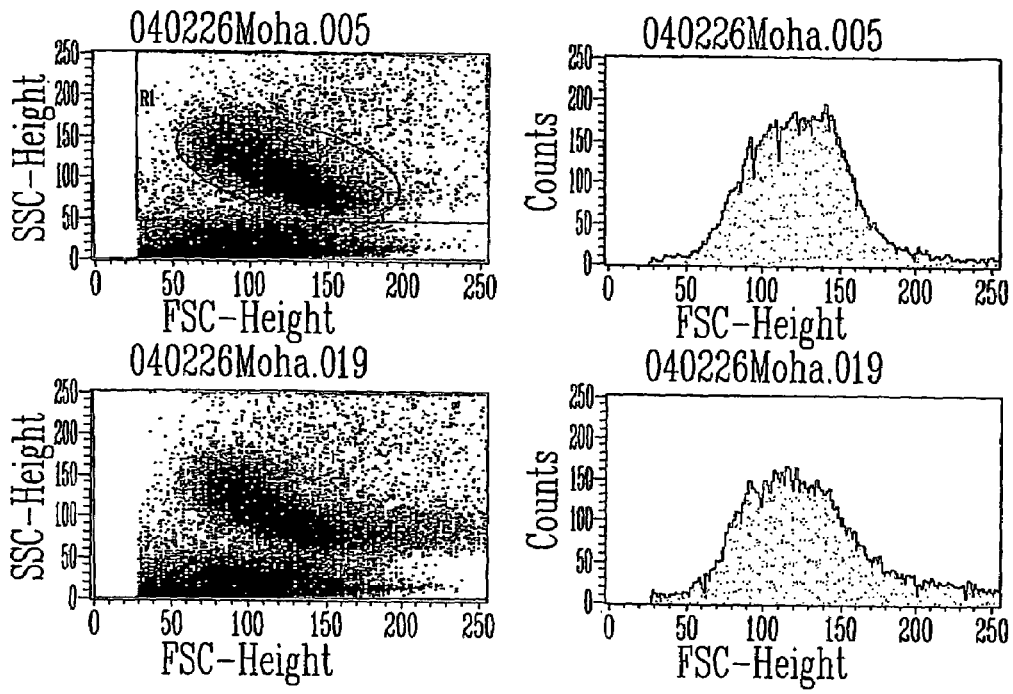
FIG. 7 illustrates a FACS analysis showing that albumin conjugated NVT-0275 is functional.
Figure 7:
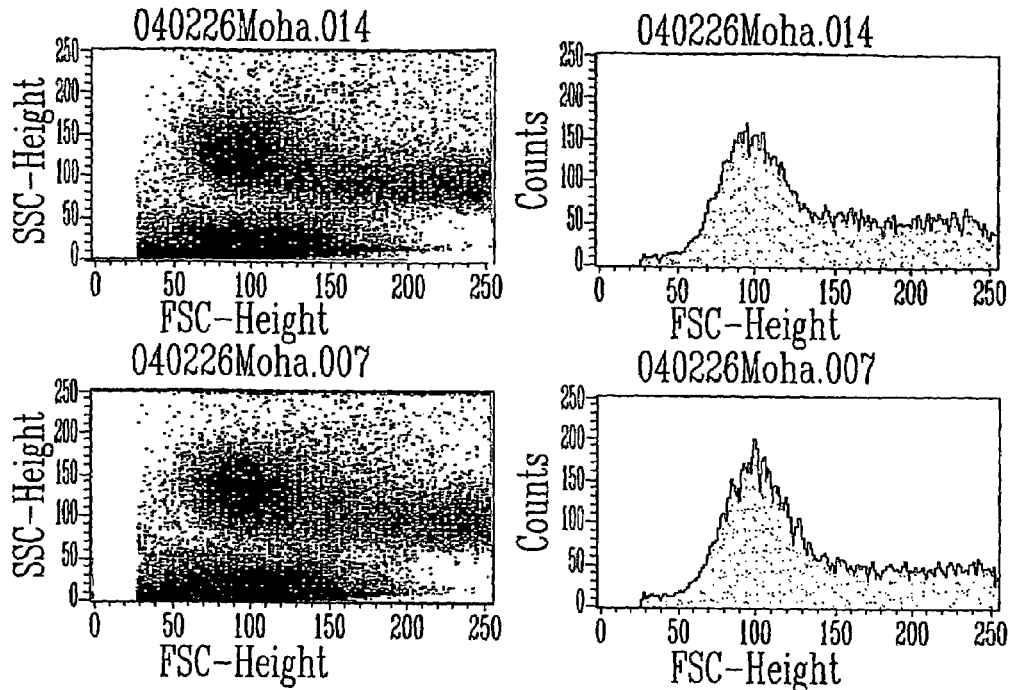

FIG. 7 shows that albumin conjugated NVT-0275 is functional. In FIG. 7, the results in each row were obtained from analysis of more than 10,000 cells. The control experiments were repeated 6 times to obtain a clear baseline. The top row shows the results from the control samples. These cells were exposed to light but not to any NVT-0275. The first panel in the first row shows the FACS (fluorescence activated cell sorting) scatter of a sample of the control cells. The second panel in the first row shows the distribution of these same cell sample and the third panel in the first row shows the statistics from the analysis of the sample. Similarly the second, third and fourth rows of the slide are results obtained using albumin conjugated NVT-0275 in concentrations of 0.155, 1.55 and 15.5 μg/ml. Notice the change in the distribution representing a greater number of smaller particles after exposure of the cells to conjugated NVT-0275.

FIG. 8 shows that EMBP conjugated NVT-0275 is fully functional. In FIG. 8, similarly as in FIG. 7, the results in each row were obtained from analysis of more than 10,000 cells. The control experiments were repeated 6 times to obtain a clear baseline. First row, first panel shows the control (WBCs received light but no NVT-0275) FACS scatter, to the right is the distribution of the cells, and the extreme right of the first row displays the statistics derived from these results. The second, third and fourth rows show results from EMBP conjugated NVT-0275 in concentrations of 0.155, 1.55 and 15.5 μg/ml.

In FIG. 8, row 4 shows dramatic results. Nearly all the cells have been pulverized to small particles by EMBP conjugated NVT-0275 and fall into the bottom part of the cell size distribution.

Figure 9:
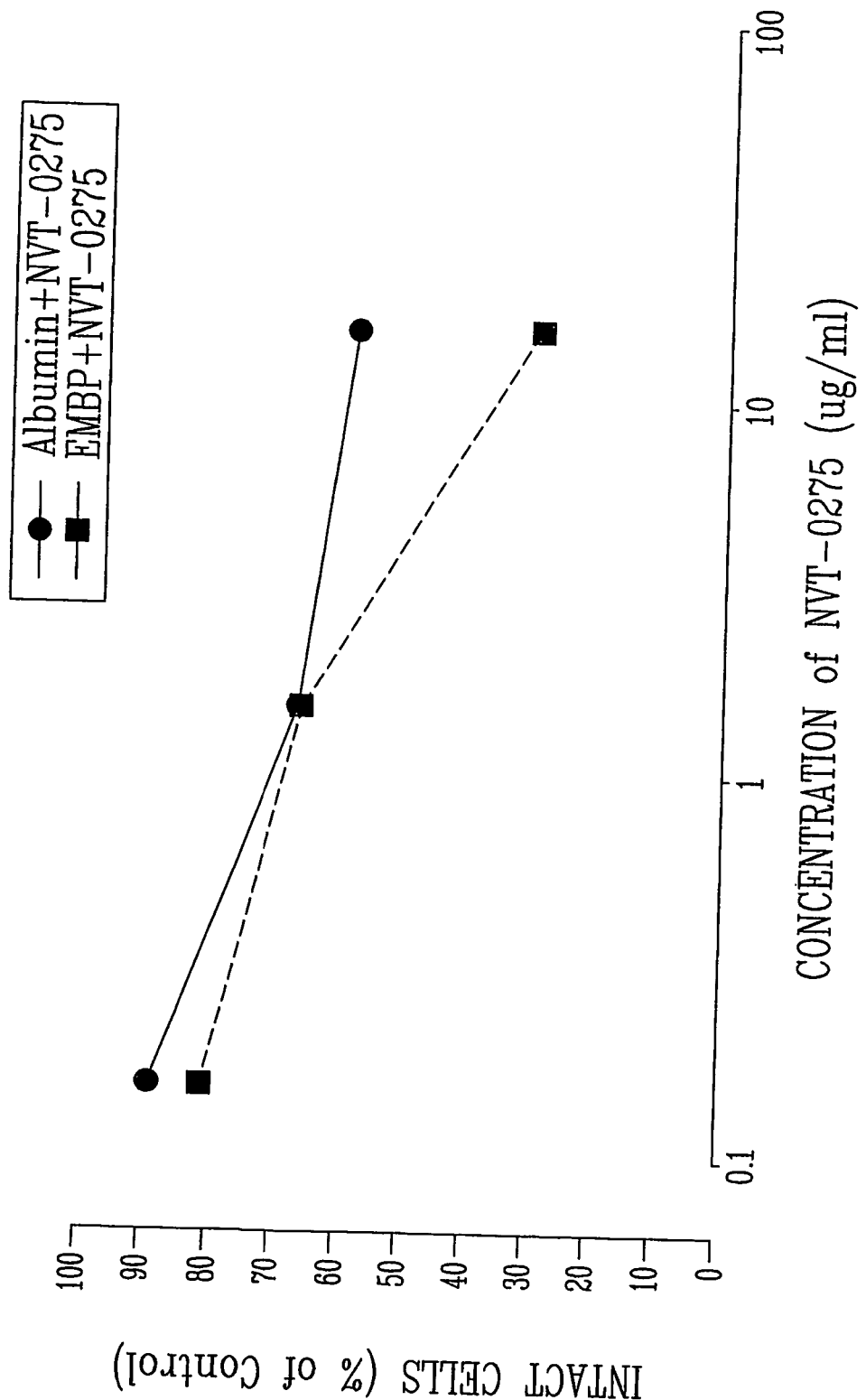
FIG. 9 illustrates the destruction of human white blood cells using one compound of the present invention conjugated to an antibody specific for eosinophils.

Thus, as summarized in FIG. 9, the results showed an inhibition that is dose dependent with the concentration of NVT-0275. Up to 80% of the cells could be destroyed by 15.5 μg/ml of EMBP conjugated NVT-0275.

It is now clearly demonstrated that conjugated NVT-0275 is fully functional and able to destroy WBCs. By increasing the concentration of NVT-0275 or the intensity or duration of exposure to light, it is expected that one would be able to destroy even more WBCs. Although albumin has some membrane binding properties, targeting NVT-0275 using specific antibody (EMBP) accumulates a greater amount of NVT-0275 on cell membranes and produces a greater destruction of cells for a given concentration of NVT-0275.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An intermediate compound consisting of 5- or 6-substituted tri-[4-(1-indolylsulfobenzo)]-mono-naphtho-porphyrazine compound of formula (II):

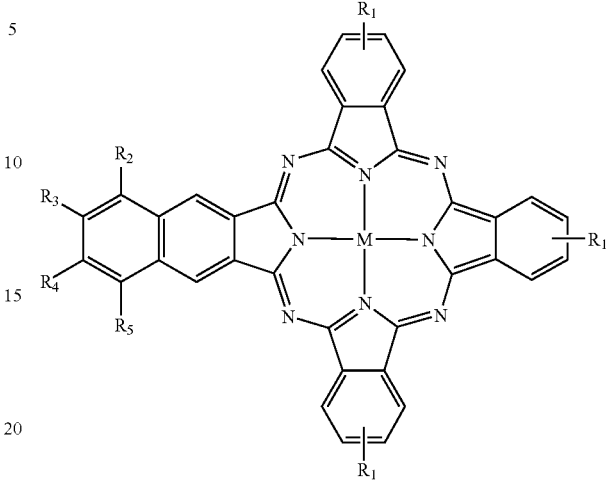

(II)

Wherein
$R_1$ is

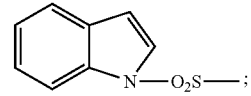

M is H . . . H or a metal; and
$R_3$, $R_4$ and $R_5$ are hydrogen when $R_2$ is an —C≡CX or —NHX when X is an alkyl, an aryl, an alkylcarboxyl or an arylcarboxyl; or
$R_2$, $R_4$ and $R_5$ are hydrogen when $R_3$ is an —C≡CX or —NHX when X is an alkyl, an aryl, an alkylcarboxyl or an arylcarboxyl.

2. A water-soluble compound of formula (III):

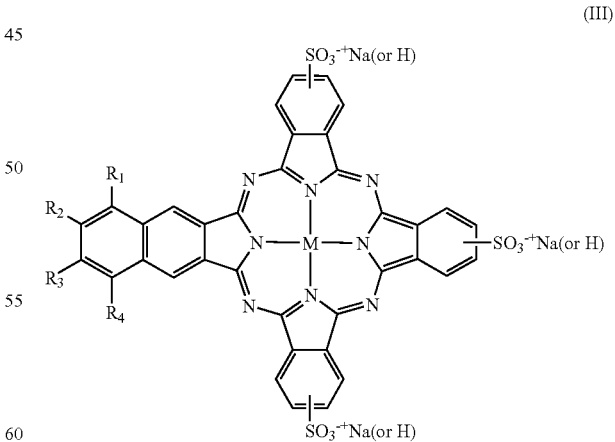

(III)

Wherein
M is H . . . H or a metal; and
$R_2$, $R_3$ and $R_4$ are hydrogen when $R_1$ is an —C≡CX or —NHX when X is an alkyl, an aryl, an alkylcarboxyl or an arylcarboxyl; or $R_1$, $R_3$ and $R_4$ are hydrogen when $R_2$ is an —C≡CX or —NHX when X is an alkyl, an aryl, an alkylcarboxyl or an arylcarboxyl.

3. The compound of claim 1, wherein M is a metal selected from the group consisting of Zn, Co(II), Ni and Cu.

4. A method for preparing the compound of claim 1, comprising the step of condensing together iodo-2,3-dicyanonaphthalene with indole protected 3,4-dicyanophenylsulfonyl in the presence of $CH_3COOM$, to obtain the compound of formula (II),

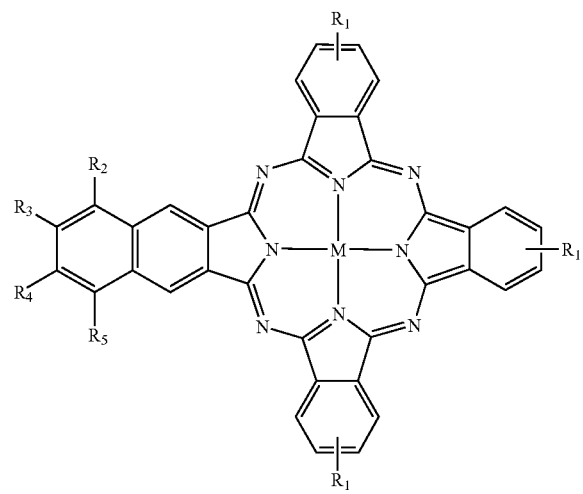

(II)

Wherein $R_1$ is

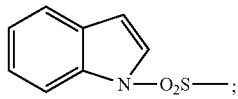

M is H . . . H or a metal selected from the group consisting of Zn, Co(II), Ni and Cu; and $R_3$, $R_4$ and $R_5$ are hydrogen when $R_2$ is an —C≡CX or —NHX when X is an alkyl, an aryl, an alkylcarboxyl or an arylcarboxyl; or $R_2$, $R_4$ and $R_5$ are hydrogen when $R_3$ is an —C≡CX or —NHX when X is an alkyl, an aryl, an alkylcarboxyl or an arylcarboxyl.

5. The method of claim 4 further comprising the step of purifying the compound of formula (II).

6. The method of claim 5, wherein the step of purifying comprises chromatography purification.

7. The method of claim 4 further comprising the step of cleaving off the indole contained in $R_1$ of the compound of formula (II) to obtain a water-soluble 5- or 6-substituted tri-(4-sulfobenzo)-mono-naphtho-porphyrazine compound of formula (III)

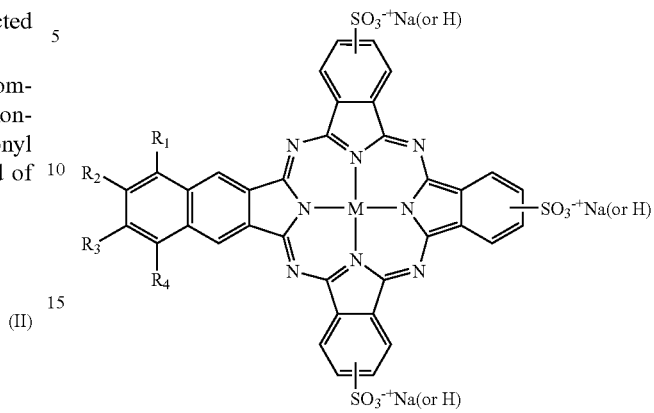

(III)

Wherein

M is H . . . H or a metal selected from the group consisting of Zn, Co(II), Ni and Cu; and $R_2$, $R_3$ and $R_4$ are hydrogen when $R_1$ is an —C≡CX or —NHX when X is an alkyl, an aryl, an alkylcarboxyl or an arylcarboxyl; or $R_1$, $R_3$ and $R_4$ are hydrogen when $R_2$ is an —C≡CX or —NHX when X is an alkyl, an aryl, an alkylcarboxyl or an arylcarboxyl.

8. The method of claim 7 further comprising the step of purifying the compound of formula (III).

9. The method of claim 8, wherein the step of purifying comprises chromatography purification.

10. An intermediate of formula (6)

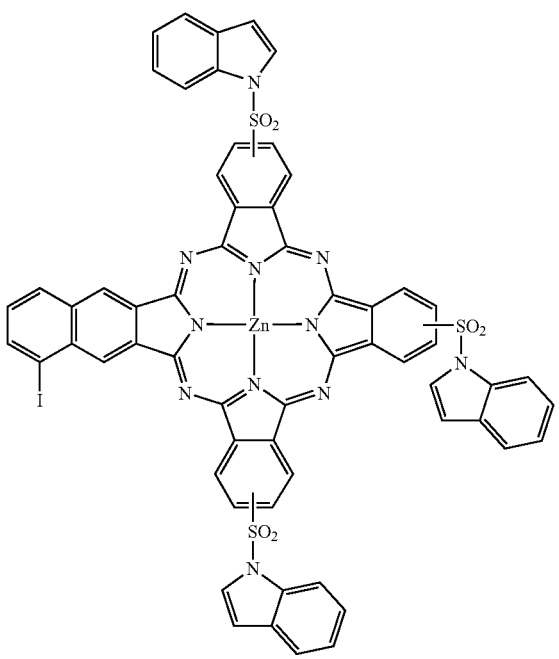

6

11. An intermediate compound of formula (16):
12. An intermediate compound of formula (21):
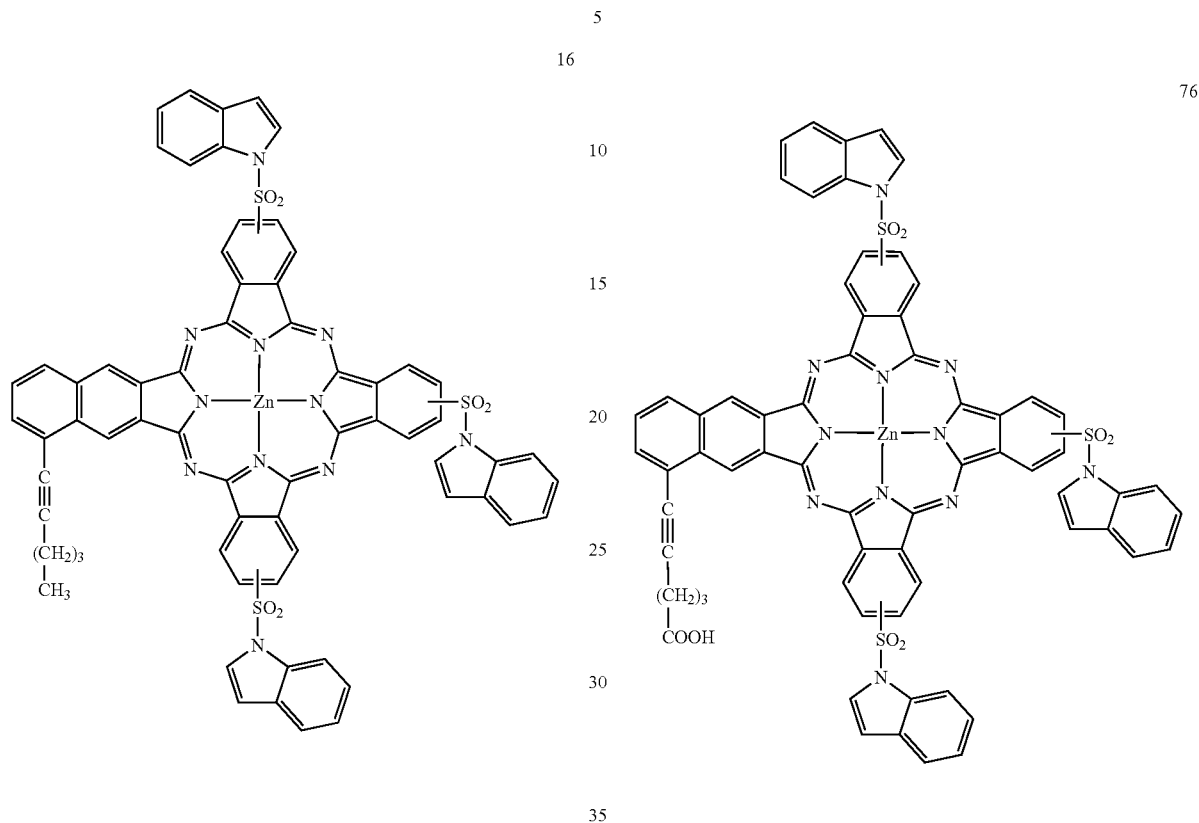
13. An intermediate compound of formula (76):
14. A compound of formula (46):
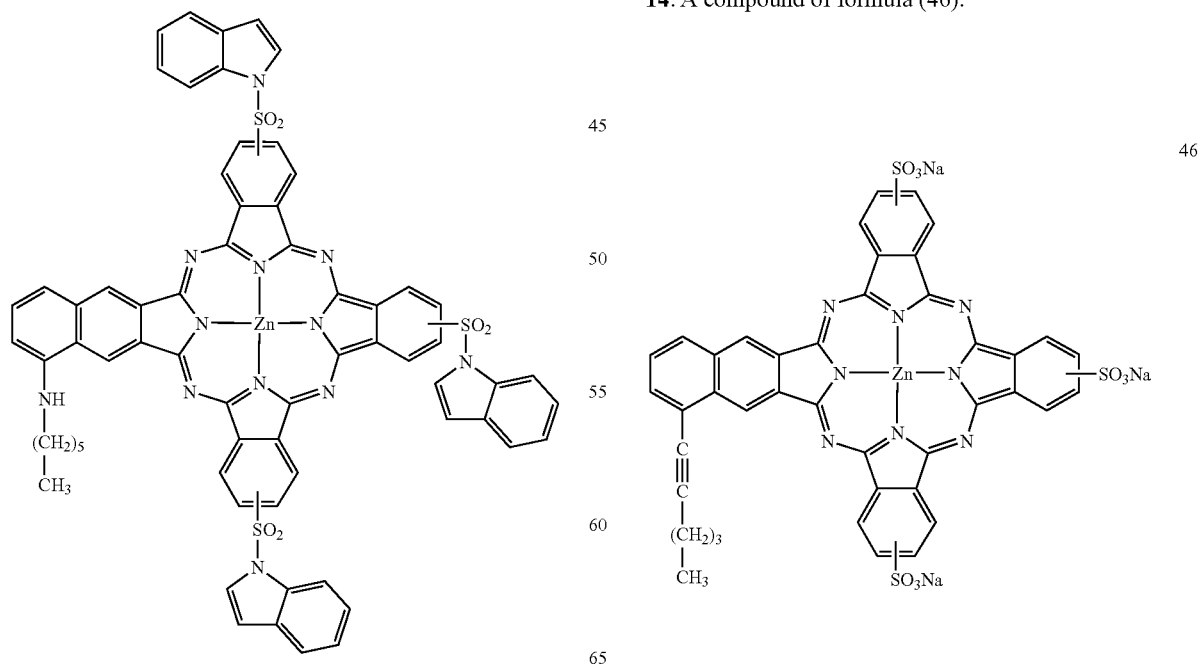

15. A compound of formula (51):
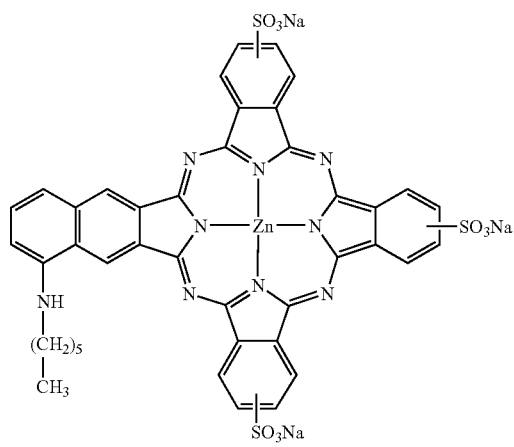
16. A compound of formula (106):
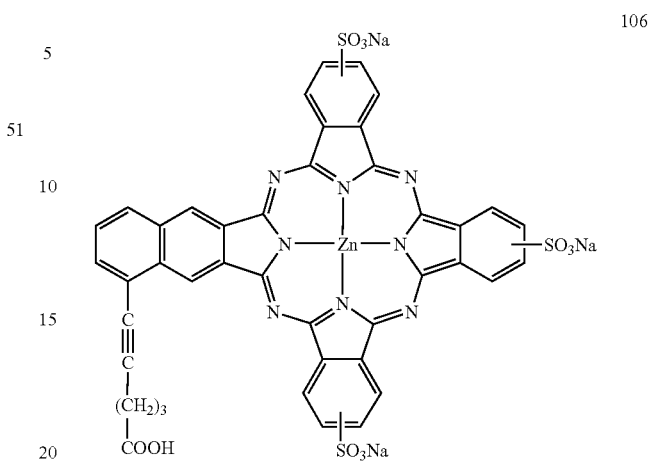
17. A conjugate comprising the compound of claim 1 conjugated to a protein carrier.
18. The conjugate of claim 17, wherein the protein carrier is an antibody.
19. The conjugate of claim 18, wherein the antibody is a monoclonal antibody.
* * * * *